US008076854B2

(12) United States Patent
Toriyama et al.

(10) Patent No.: US 8,076,854 B2
(45) Date of Patent: Dec. 13, 2011

(54) LIGHT SOURCE APPARATUS

(75) Inventors: Seiki Toriyama, Tokyo (JP); Mutsumi Oshima, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 414 days.

(21) Appl. No.: 12/355,006

(22) Filed: Jan. 16, 2009

(65) Prior Publication Data

US 2009/0212723 A1   Aug. 27, 2009

(30) Foreign Application Priority Data

Feb. 25, 2008   (JP) .................................. 2008-043196

(51) Int. Cl.
*H01K 7/00* (2006.01)
(52) U.S. Cl. .............................. 315/76; 315/82; 315/362
(58) Field of Classification Search ..................... 315/76, 315/82–84, 362
See application file for complete search history.

(56) References Cited

U.S. PATENT DOCUMENTS 5,230,555 A    7/1993  Stephenson et al.
5,829,866 A *  11/1998 Stegeman ..................... 362/655
2005/0146688 A1* 7/2005 Takemi ........................... 353/87

FOREIGN PATENT DOCUMENTS

FR   2 734 625     11/1996
JP   06-175043     6/1994

OTHER PUBLICATIONS

Extended European Search Report dated Aug. 30, 2010.

* cited by examiner

*Primary Examiner* — Anh Tran
(74) *Attorney, Agent, or Firm* — Scully, Scott, Murphy & Presser, P.C.

(57) ABSTRACT

A light source apparatus includes: a lamp replacement door configured to open and close a lamp replacement window; an igniter replacement door configured to open and close an igniter replacement window which is opened at a position different from the position of the lamp replacement window; a door opening detection switch configured to detect the opening and closing of the lamp replacement door; a circuit breaker device configured, when the opening state of the lamp replacement door is detected by the door opening detection switch, to interrupt power supply to an electric circuit; and a door opening regulation mechanism configured to lock the closing state of the igniter replacement door, and configured to permit the opening of the igniter replacement door.

15 Claims, 21 Drawing Sheets

LIGHT SOURCE APPARATUS

This application claims benefit of Japanese Application No. 2008-043196 filed in Japan on Feb. 25, 2008, the contents of which are incorporated by this reference.

BACKGROUND OF THE INVENTION

1. Field of the Invention

The present invention relates to a light source apparatus configured to prevent a second door from being opened when a first door is closed.

2. Description of the Related Art

Conventionally, a discharge lamp, such as a xenon lamp, which generates high luminance light, is provided as a light source of a light source apparatus for supplying illumination light to an endoscope, a projector, and the like. Further, between the discharge lamp and a lamp power source, there is provided an igniter for temporarily boosting the electric power supplied from the lamp power source to a high voltage. When the boosted high voltage is applied to the discharge lamp, a discharge is started in the discharge lamp, so that the discharge lamp is turned on.

In the case where consumables, such as the discharge lamp used in the light source apparatus are intended to be replaced, as disclosed in, for example, Japanese Patent Application Laid-Open Publication No. 6-175043, after a lamp replacement door (first door) of the light source apparatus is opened, the discharge lamp is taken out together with a heat sink which holds the discharge lamp, so as to be replaced with a new discharge lamp, and thereafter the new discharge lamp is again housed in the light source apparatus. In this case, when the lamp replacement door is opened, a circuit breaker device is operated, so as to interrupt the power source circuit.

On the other hand, the igniter is also a consumable, but the igniter is provided in the inside of the light source apparatus because the igniter has a longer life and a lower frequency of replacement as compared with the discharge lamp. Therefore, when the igniter is replaced, a top cover is first removed, and then the igniter is taken out after a shield case covering the igniter is removed.

SUMMARY OF THE INVENTION

A light source apparatus according to the present invention includes:

an apparatus main body;

a first opening portion provided in the apparatus main body, and a first door configured to open and close the first opening portion;

a second opening portion provided in the apparatus main body at a position different from the position of the first opening portion, and a second door configured to open and close the second opening portion;

an opening and closing detecting portion configured to detect the opening and closing of the first door;

a circuit breaker device configured, when the opening state of the first door is detected by the opening and closing detecting portion, to interrupt power supply to a circuit in the apparatus main body; and a door opening regulation mechanism configured, when the closing state of the first door is detected by the opening and closing detecting portion, to lock the closing state of the second door, and configured, when the opening state of the first door is detected by the opening and closing detecting portion, to permit the opening of the second door.

According to such configuration, when the first door is not opened, the door opening regulation mechanism prevents the lock of the second door from being released. Thus, when the second door is opened, the power source circuit can be interrupted by the circuit breaker switch on the side of the first door without provision of circuit breaker switches on both sides of the first door and the second door. As a result, it is possible to realize the reduction in the number of components by sharing the components, and possible to realize the simplification of the electrical wiring and assembling.

BRIEF DESCRIPTION OF THE DRAWINGS

FIG. 1 to FIG. 14 show a first embodiment according to the present invention, in which:

FIG. 1 is an overall perspective view of a light source apparatus;

FIG. 2 is a perspective view in the state where a top cover of the light source apparatus is removed;

FIG. 3 is a perspective view of a chassis in which a lamp case is provided;

FIG. 4 is a perspective view of the chassis viewed from the bottom surface;

FIG. 5 is a sectional view taken along the line V-V in FIG. 1;

FIG. 6 is a sectional view in the state where a lamp replacement door is removed in the state shown in FIG. 5;

FIG. 7 is a sectional view taken along the line VII-VII in FIG. 6;

FIG. 8 is a bottom view of a lamp base in which an igniter substrate is omitted, in the state where the lamp replacement door is closed;

FIG. 9 is a bottom view of the lamp base in which the igniter substrate is omitted, in the state where the lamp replacement door is opened;

FIG. 10 is a perspective view corresponding to FIG. 3, in the state where the lamp case is removed;

FIG. 11 is a perspective view corresponding to FIG. 10, in the state where the lamp base is removed and at the time when the lamp replacement door is closed;

FIG. 12 is a perspective view corresponding to FIG. 10, in the state where the lamp base is removed and at the time when the lamp replacement door is opened;

FIG. 14 is a sectional view taken along the line XIV-XIV in FIG. 8.

FIG. 15 to FIG. 20 show a second embodiment according to the present invention, in which:

FIG. 15 is a sectional view corresponding to FIG. 5;

FIG. 16 is a sectional view corresponding to FIG. 6;

FIG. 17 is a sectional view taken along the line XVII-XVII in FIG. 15;

FIG. 18 is a sectional view taken along the line XVIII-XVIII in FIG. 16;

FIG. 19 is a sectional view corresponding to FIG. 16, in the state where both of a lamp replacement door and an igniter replacement door are opened; and FIG. 20 is a sectional view taken along the line XX-XX in FIG. 19.

DETAILED DESCRIPTION OF THE PREFERRED EMBODIMENTS

In the following, embodiments according to the present invention will be described with reference to the accompanying drawings.

First Embodiment

FIG. 1 to FIG. 14 show a first embodiment according to the present invention. Note that in the following, the right and left directions will be explained by taking the front view as a reference.

Figure 1:
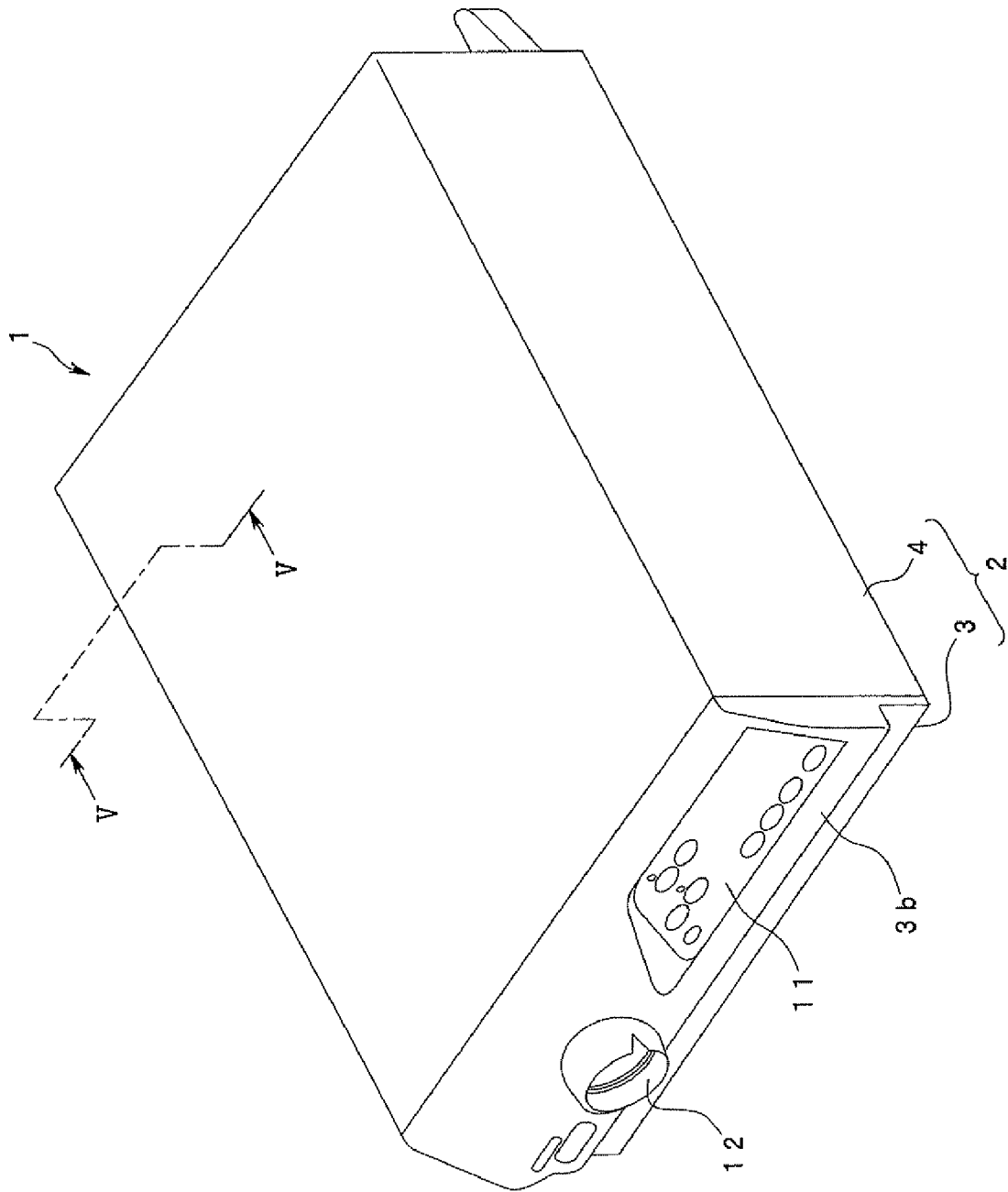
Figure 2:
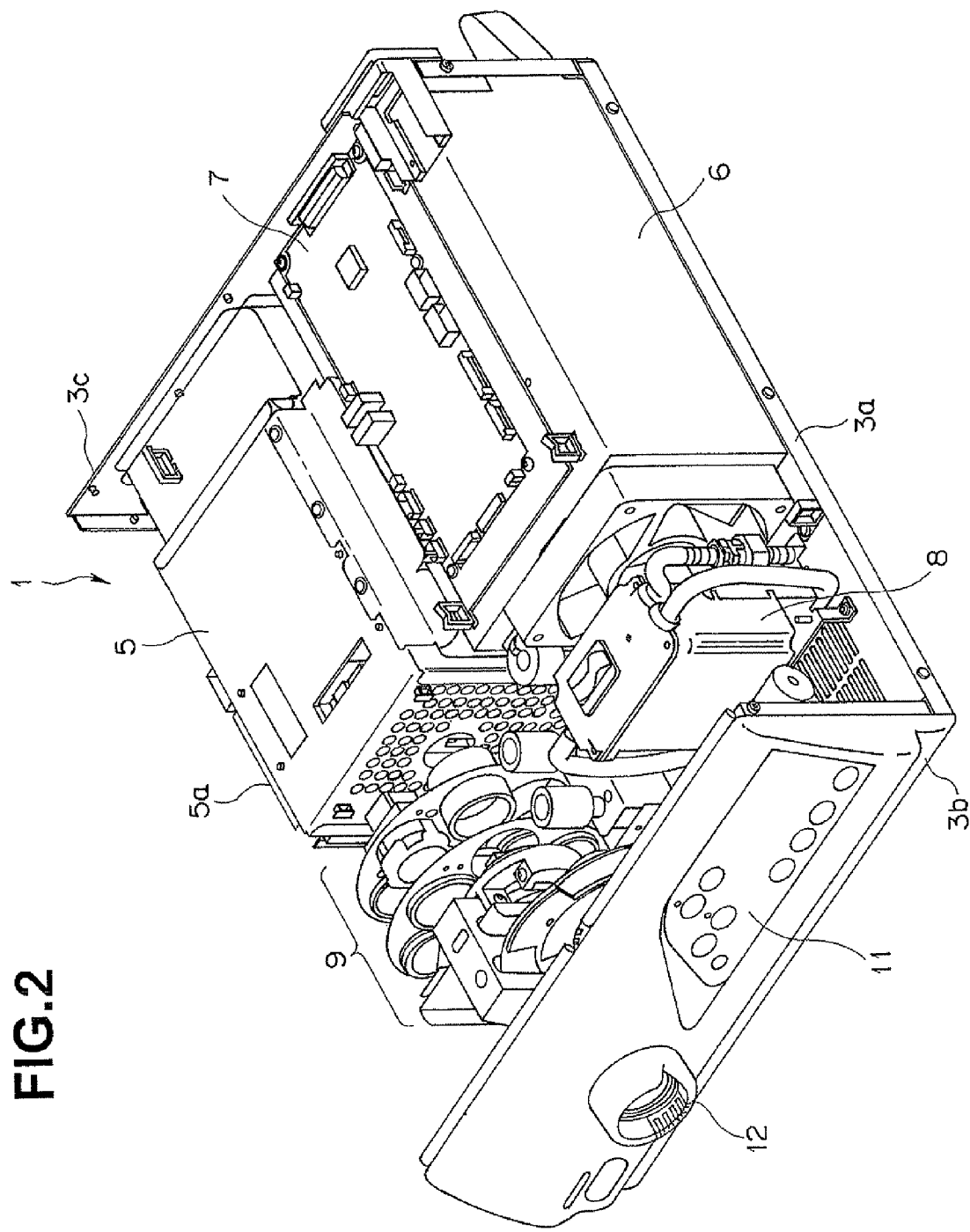

Reference numeral 1 in FIG. 1 and FIG. 2 denotes a light source apparatus which supplies illumination light to, for example, an endoscope. An apparatus main body 2 of the light source apparatus 1 has a main body portion 3 and a top cover 4. The main body portion 3 is formed approximately in a U-shape, in which a front panel 3b is fixed to a front portion of a chassis 3a, in which a rear plate 3c is fixed to a rear portion of the chassis 3a, and in which the upper surface and both side surfaces are opened. On the other hand, the top cover 4 is formed approximately in a U-shape so as to cover the upper surface, and the left and right side surfaces of the main body portion 3.

Further, in the rear left and right portions of the chassis 3a, there are provided a lamp case 5 configured to house a lamp unit, and a power source case 6 configured to house a power source unit which supplies power to each of drive portions. Further, a control board 7 configured to perform overall control of the light source apparatus 1 is fixed to the upper surface of the power source case 6. Further, an optical system 9 is provided in front of the lamp case 5, and an air supply pump 8 is provided in front of the power source case 6.

Further, an operation portion 11 and a socket portion 12 are provided in the front panel 3b. In the operation portion 11, there are provided at predetermined positions various switches such as a power source switch, a switch for adjusting the light quantity of illumination light emitted from a discharge lamp housed in the lamp case 5, a switch for adjusting a diaphragm arranged in the optical system 9, and a pump switch for switching the operation and stop of the air supply pump 8. Further, there is attached to the socket portion 12, a light guide connector (not shown) fixed to an end portion of a universal cord extended from an endoscope which is not shown.

When the light guide connector is attached to the socket portion 12, the illumination light from the discharge lamp housed in the lamp case 5 can be made incident, via the optical system 9, on the incident end surface of a light guide fiber projecting from the light guide connector. Further, an air supply tube projecting from the light guide connector is connected to an air supply conduit (not shown) extended from the air supply pump 8, so that the air can be supplied.

Figure 3:
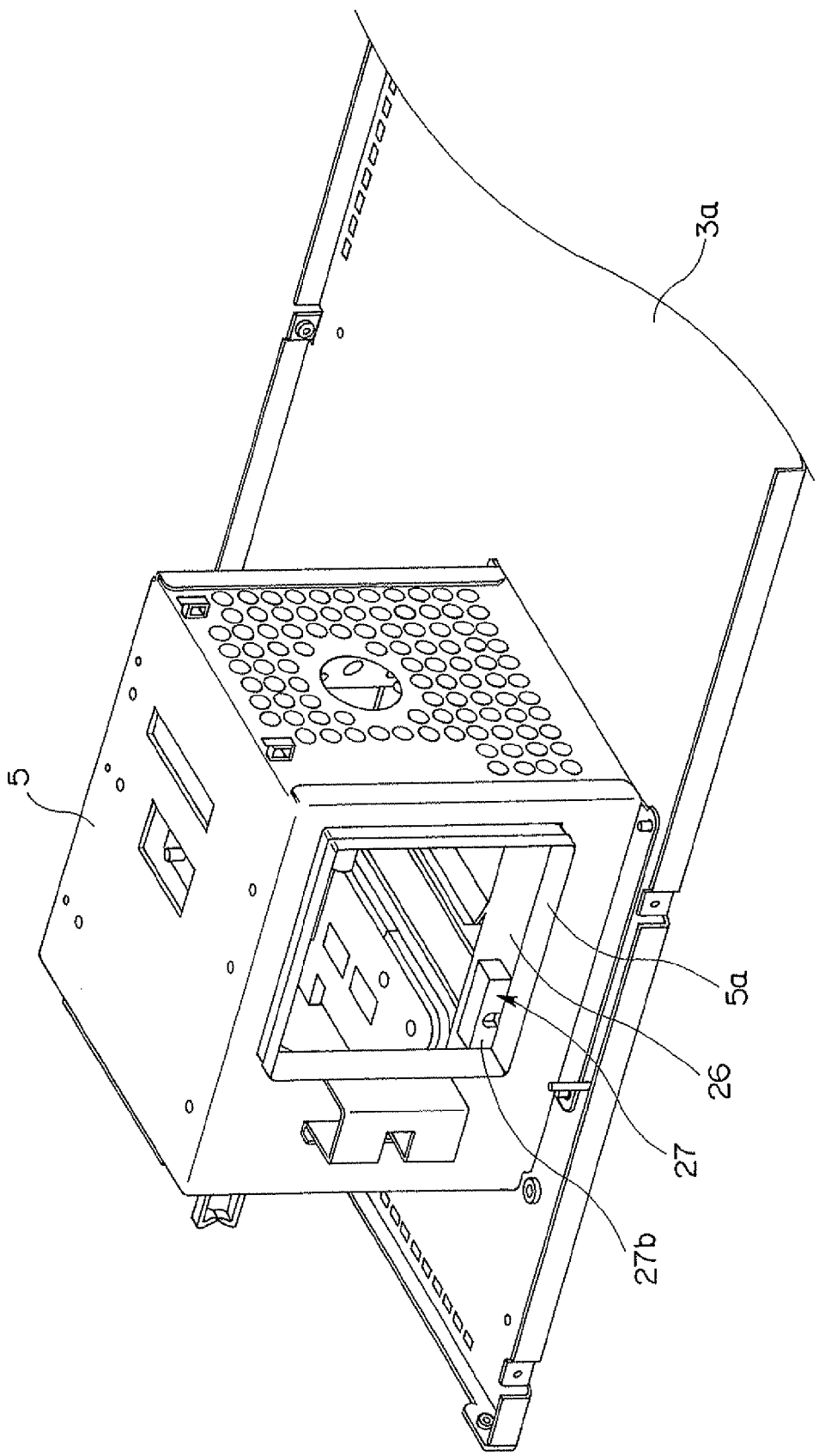
Figure 5:
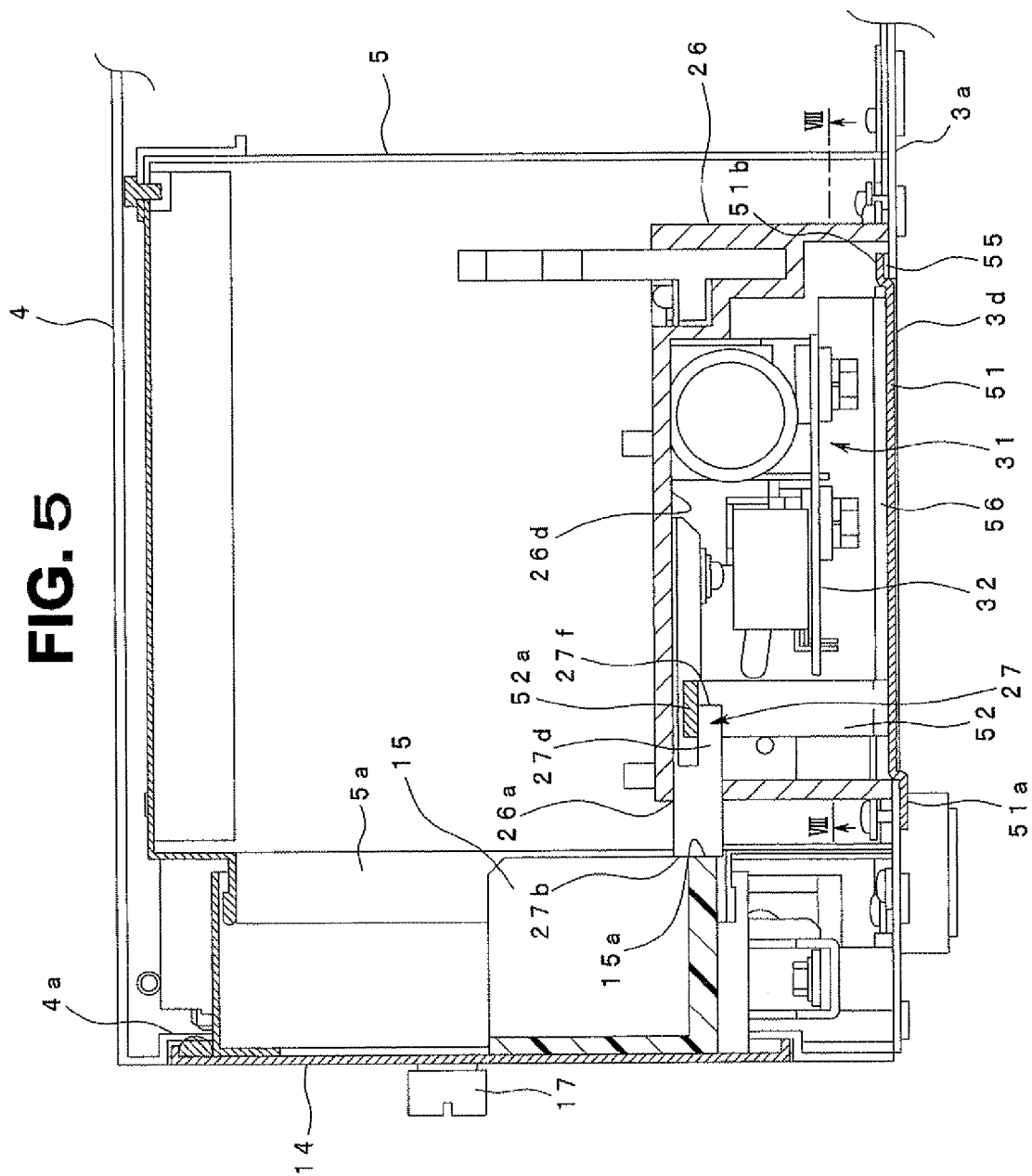
Figure 6:
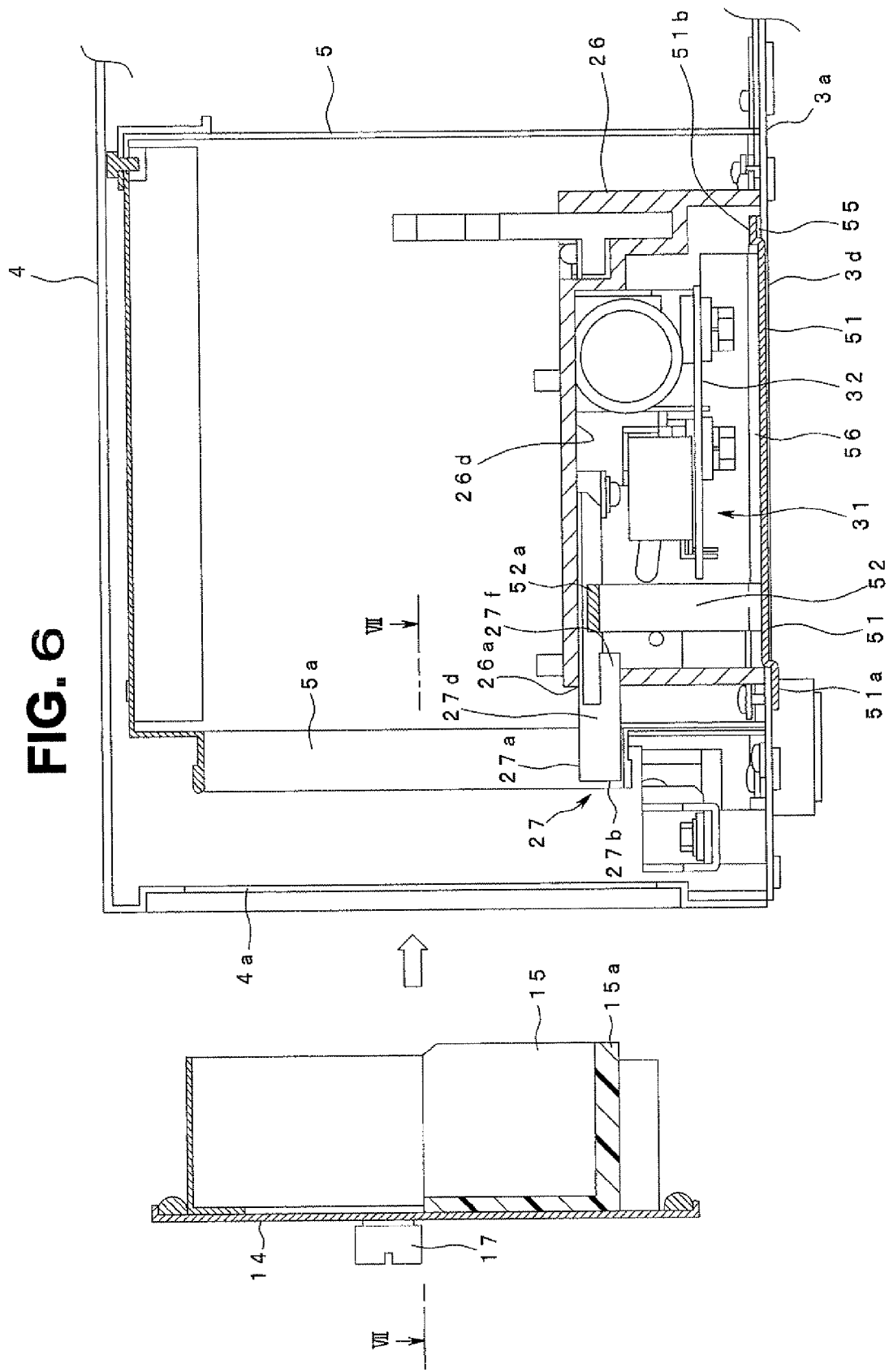
Figure 7:
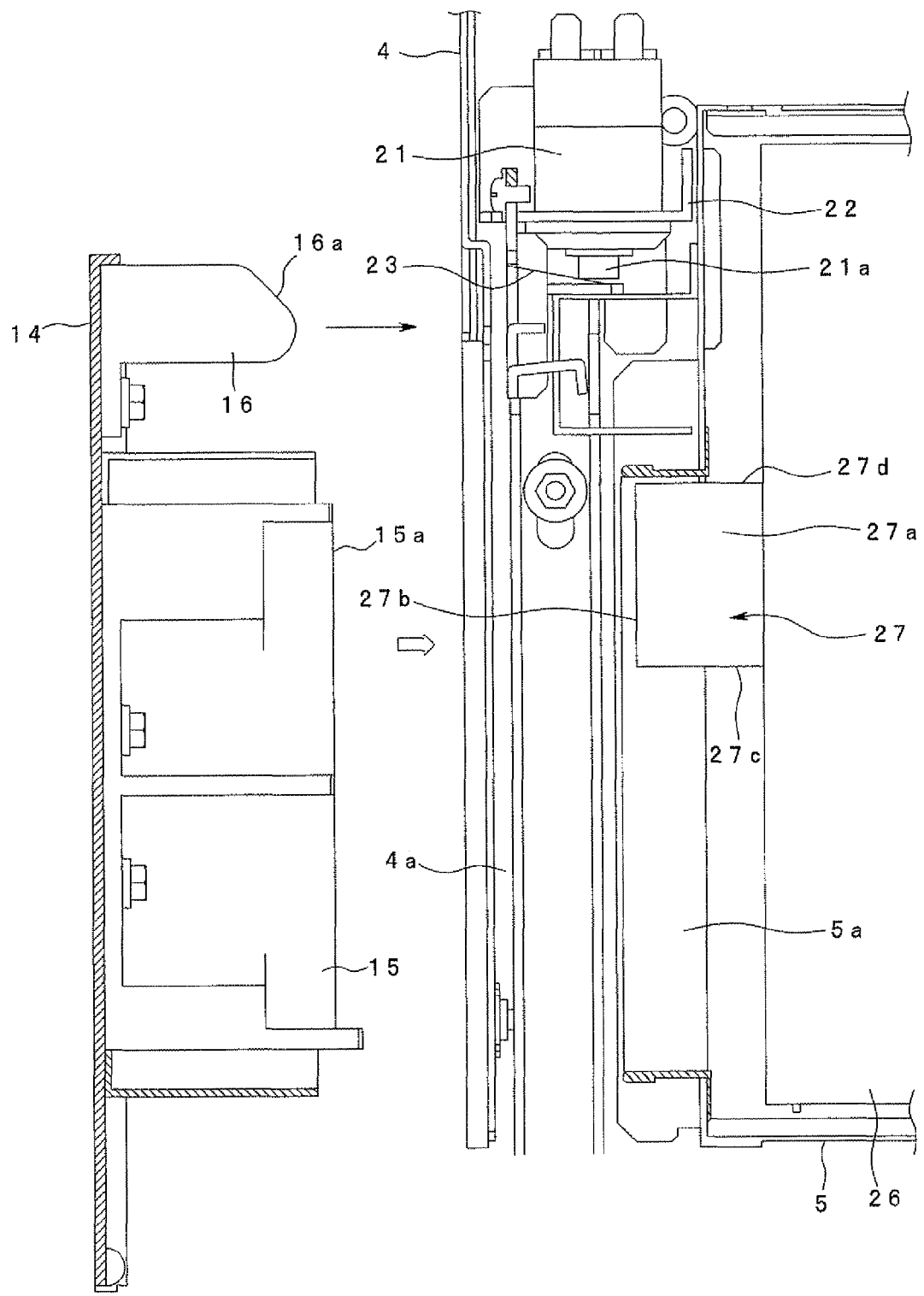

As shown in FIG. 3, the lamp case 5 has a shielding function, and an opening window 5a is formed in the left side surface of the lamp case 5. Further, as shown in FIG. 5 to FIG. 7, a lamp replacement window 4a as a first opening portion, which enables the lamp unit to be accessed from the outside via the opening window 5a, is formed in the surface of the top cover 4, which faces the opening window 5a, that is, in the left side surface of the top cover 4. The lamp replacement window 4a is closed by a lamp replacement door 14 as a first door.

A protection member 15 and a switch pressing member 16 are fixed to the inner surface of the lamp replacement door 14. Both of the members 15 and 16 are formed of an insulating material, such as a resin. In the present embodiment, the switch pressing member 16 is fixed to one side (on the deep side in the figure) of the lamp replacement door 14. The switch pressing member 16 is projected in the direction of the lamp replacement window 4a formed in the top cover 4, and a taper guide surface 16a is formed at the distal end portion of the switch pressing member 16.

When the lamp replacement door 14 is attached to the lamp replacement window 4a formed in the top cover 4, and when the lamp replacement door 14 is screwed to the top cover 4 via a thumb screw 17, the switch pressing member 16 is made to penetrate the lamp replacement window 4a which is opened in the top cover 4, so as to face the inside of the apparatus main body 2. A lamp replacement door opening detection switch 21, as an opening and closing detecting portion, is arranged at a position at which the switch pressing member 16 is made to face the inside of the apparatus main body 2, and which is between the lamp case 5 and the top cover 4. The lamp replacement door opening detection switch 21 is a twin switch having an interlock switch and a discharge switch, and is fixed to the chassis 3a via a bracket 22.

When the lamp replacement door opening detection switch 21 detects the opening and closing of the lamp replacement door 14, and when the lamp replacement door 14 is opened, the interlock switch is turned off. Thereby, the power source circuit of the power source unit housed in the power source case 6 is interrupted by a known circuit breaker device connected to the interlock switch, so that the power supply to the electric circuit in the apparatus main body 2 is interrupted. At the same time, the discharge switch is turned on to make a discharging circuit connected, so that the residual voltage in the electric circuit is released. Further, when the lamp replacement door 14 is closed, the interlock switch is turned on, so that the power source circuit is connected to make the discharge switch turned off.

Further, a switch pressing portion 21a provided in the lamp replacement door opening detection switch 21 is arranged at a position at which the switch pressing portion 21a is brought into slide contact with the taper guide surface 16a formed on the switch pressing member 16 so as to be pressed by the taper guide surface 16a. Further, the free end side of a leaf spring guide 23 is brought into contact with the switch pressing portion 21a. The fixed end side of the leaf spring guide 23 is fixed by being substantially horizontally extended toward the left side surface of the chassis 3a.

When the switch pressing member 16 is made to penetrate the lamp replacement window 4a to face the inside of the apparatus main body 2, the taper guide surface 16a formed at the distal end portion of the switch pressing member 16 presses the leaf spring guide 23, so that the switch pressing portion 21a of the lamp replacement door opening detection switch 21 is pressed via the leaf spring guide 23. Then, the lamp replacement door opening detection switch 21 is turned on, so that the power source case 6 is brought into the state of being able to supply electric power. On the other hand, when the switch pressing member 16 is extracted from the lamp replacement window 4a, the pressing force against the switch pressing portion 21a is released. Thereby, the lamp replacement door opening detection switch 21 is turned off, so that the power supply from the power source case 6 is interrupted. Note that the above described leaf spring guide 23 has both a function of guiding the switch pressing member 16 to the switch pressing portion 21a, and a function of amplifying the switching operation of the switch pressing portion 21a.

Further, a lamp base 26 is arranged in the lamp case 5. The lamp base 26 is formed of a material, such as a ceramic material, having high heat transfer and insulating properties, and is fixed to the chassis 3*a* by using a screw, and the like.

A known lamp unit (not shown) is fixed on the lamp base 26. The lamp unit is configured so as to be freely taken out from the opening window 5*a* which is opened in the lamp case 5. A negative side heat sink and a positive side heat sink are provided in the lamp unit, and the discharge lamp is detachably held between both the heat sinks. The heat sinks are connected to a negative electrode 35*a* and a positive electrode 35*b* (see FIG. 10) which are vertically erected on the lamp base 26.

As shown in FIG. 3, FIG. 5, FIG. 6 and FIG. 10, the lamp base 26 is formed in a box shape which has a predetermined height and the lower portion of which is opened. The opening end edge of the lamp base 26 is fixed to the chassis 3*a*. The upper surface of the lamp base 26 is formed at a position higher than the lower edge portion of the opening window 5*a* formed in the lamp case 5, and a guide hole portion 26*a* is formed in the side surface of the lamp base 26, which is exposed from the opening window 5*a*. A slider 27 is inserted into the guide hole portion 26*a* so as to be freely moved forward and backward.

The slider 27 is formed of an insulating material, such as a resin. As shown in FIG. 13A to FIG. 13E, the slider 27 has a rectangular flat upper surface 27*a*, and a front surface portion 27*b* is formed at the front end of the upper surface 27*a*. A side surface portion 27*c* is formed on one side of the upper surface 27*a*, and a side surface block portion 27*d* is formed on the other side. A stopper portion 27*e* is notched and formed on the front surface portion 27*b* side of the side surface portion 27*c*. Further, a claw portion 27*f* projecting backward is formed in the rear end portion of the side surface block portion 27*d*. Further, a shaft portion 27*g* is extended backward from the front surface portion 27*b* along the rear surface of the upper surface 27*a*, and a snap ring 28 is fitted to the extended end portion of the shaft portion 27*g*. Further, a return spring 29 is inserted into the shaft portion 27*g*.

Figure 13A:
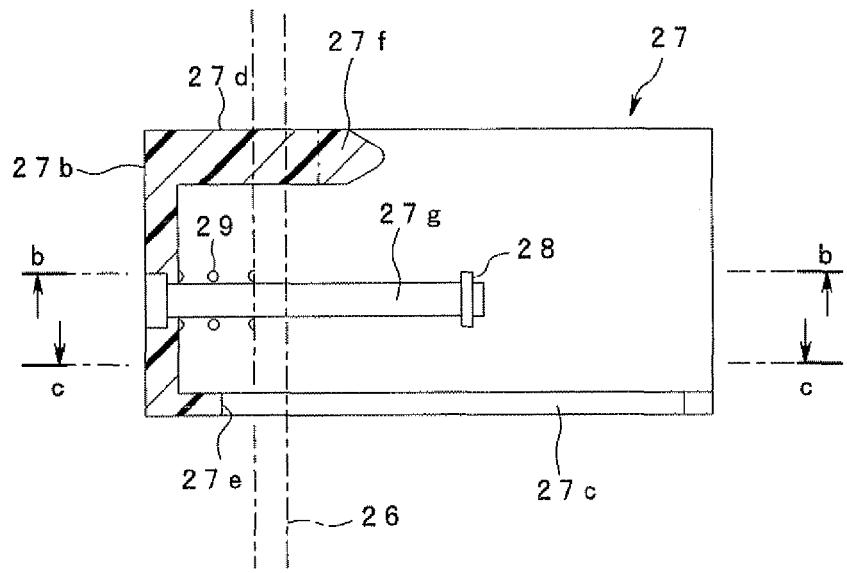
FIG. 13A shows a slider and is a sectional view taken along the line a-a in FIG. 13D.
Figure 13B:
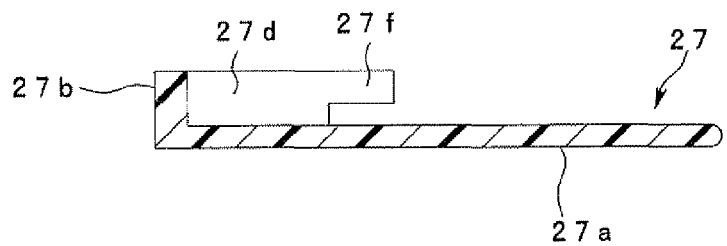
FIG. 13B is a sectional view taken along the line b-b in FIG. 13A.
Figure 13C:
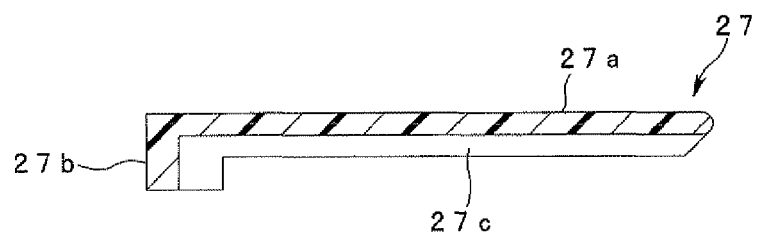
FIG. 13C is a sectional view taken along the line c-c in FIG. 13A.
Figure 13D:
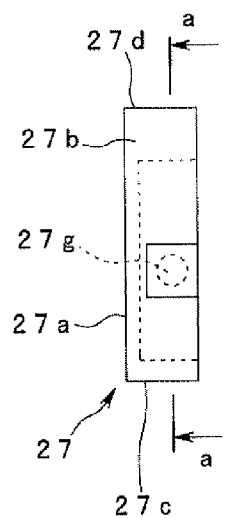
FIG. 13D is a front view of the slider.
Figure 13E:
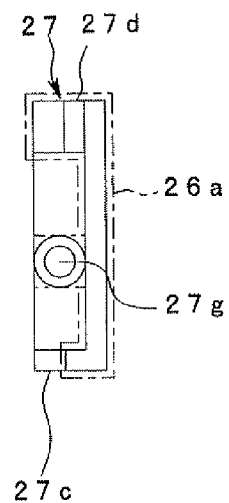
FIG. 13E is a rear view of the slider.
Figure 13F:
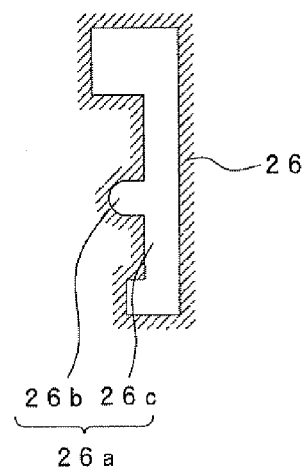
FIG. 13F is a front view of a guide hole portion in which a discharge lamp is inserted.

As shown in FIG. 13F, the guide hole portion 26*a* formed in the lamp base 26 has a substantially U-shaped main body insertion hole portion 26*b* in which the upper surface 27*a*, the side surface portion 27*c*, and the side surface block portion 27*d* of the slider 27 are inserted, and has a shaft insertion hole portion 26*c* formed in a U-shaped groove which communicates with the main body insertion hole portion 26*b*, and in which the shaft portion 27*g* is inserted. The shaft insertion hole portion 26*c* is formed to have a groove diameter which is larger than the diameter of the shaft portion 27*g*, and which is smaller than the diameter of the snap ring 28.

In order to attach the slider 27 to the guide hole portion 26*a*, the return spring 29 is first inserted into the shaft portion 27*g*, and thereafter the upper surface 27*a*, the side surface portion 27*c*, and the side surface block portion 27*d* are inserted into the main body insertion hole portion 26*b*. Further, the shaft portion 27*g* is inserted into the shaft insertion hole portion 26*c*. Then, the snap ring 28 is fitted to the end portion of the shaft portion 27*g* which is made to penetrate the shaft insertion hole portion 26*c* to project to the inner surface of the lamp base 26. Thereby, the assembling is completed. Note that slider guides 26*e* and 26*f* for guiding the width direction of the slider 27 are projectingly provided on a ceiling surface 26*d* in the lamp base 26.

Figure 8:
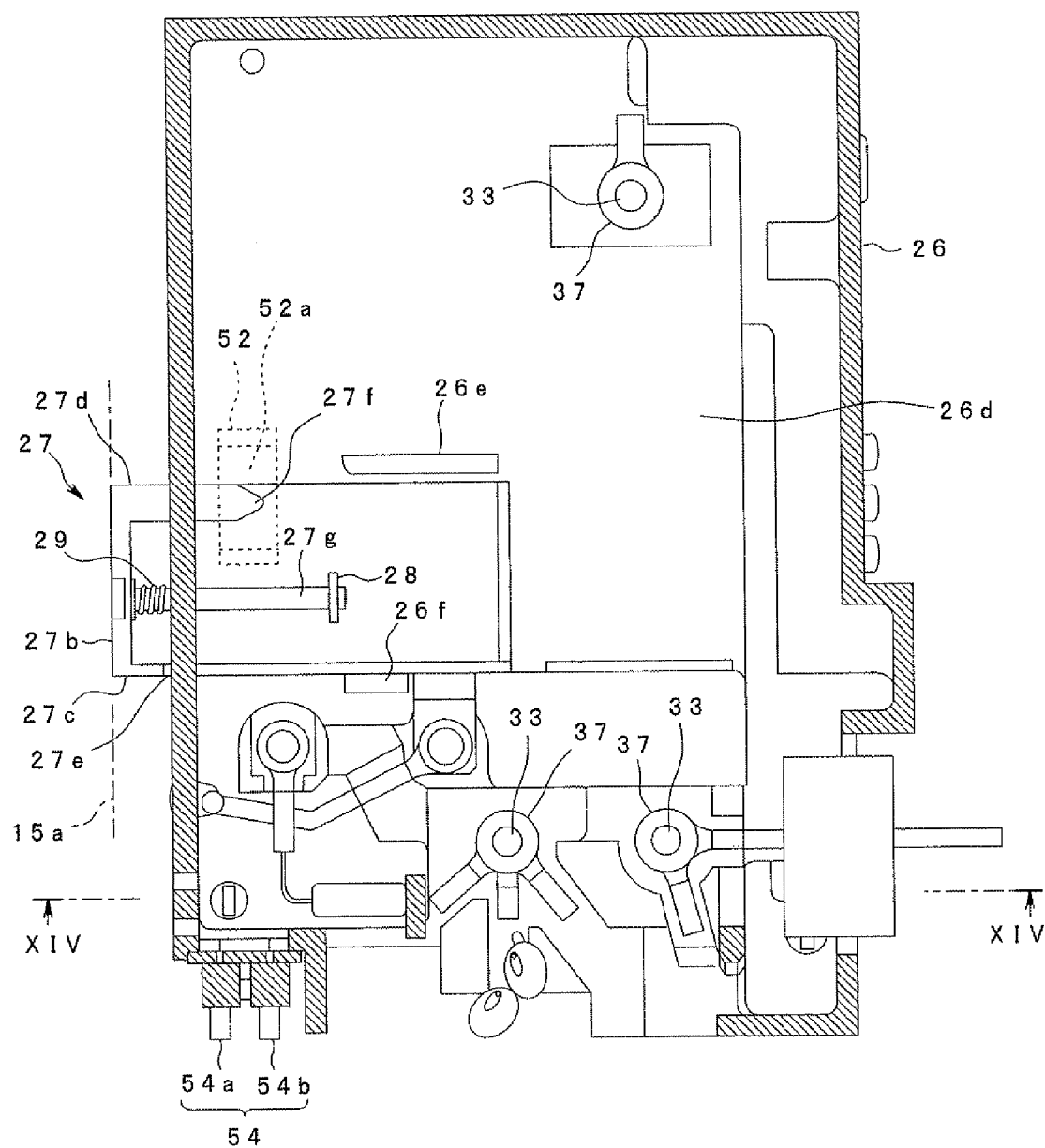

When the slider 27 is attached at a predetermined position with respect to the guide hole portion 26*a* as shown in FIG. 8, the return spring 29 inserted in the shaft portion 27*g* is held between the inner surface of the front surface portion 27*b* of the slider 27 and the side surface of the lamp base 26, so that the slider 27 is ejected from the side surface of the lamp base 26 by an elastic repulsive force of the return spring 29. Note that the snap ring 28 is fitted to the end portion of the shaft portion 27*g*, and hence the slider 27 is prevented from coming off from the guide hole portion 26*a*. Further, when the slider 27 is pressed and moved into the lamp base 26, the stopper portion 27*e* formed in the side surface portion 27*c* is hooked on the side surface of the lamp base 26, so that the stroke end in the backward movement is regulated. Further, the slider guides 26*e* and 26*f* are provided so as to face both side surfaces of the slider 27, and the upper surface 27*a* is set close to the ceiling surface 26*d* of the lamp base 26, so that the slider 27 is smoothly moved forward and backward by being guided by the three surfaces.

When the lamp replacement window 4*a* is closed by the lamp replacement door 14, a pressing surface 15*a* formed on the protection member 15 fixed to the inner surface of the lamp replacement door 14 is brought into contact with the slider 27, so as to press and retract the slider 27. The stroke at this time is set shorter than the stroke end set beforehand.

Figure 14:
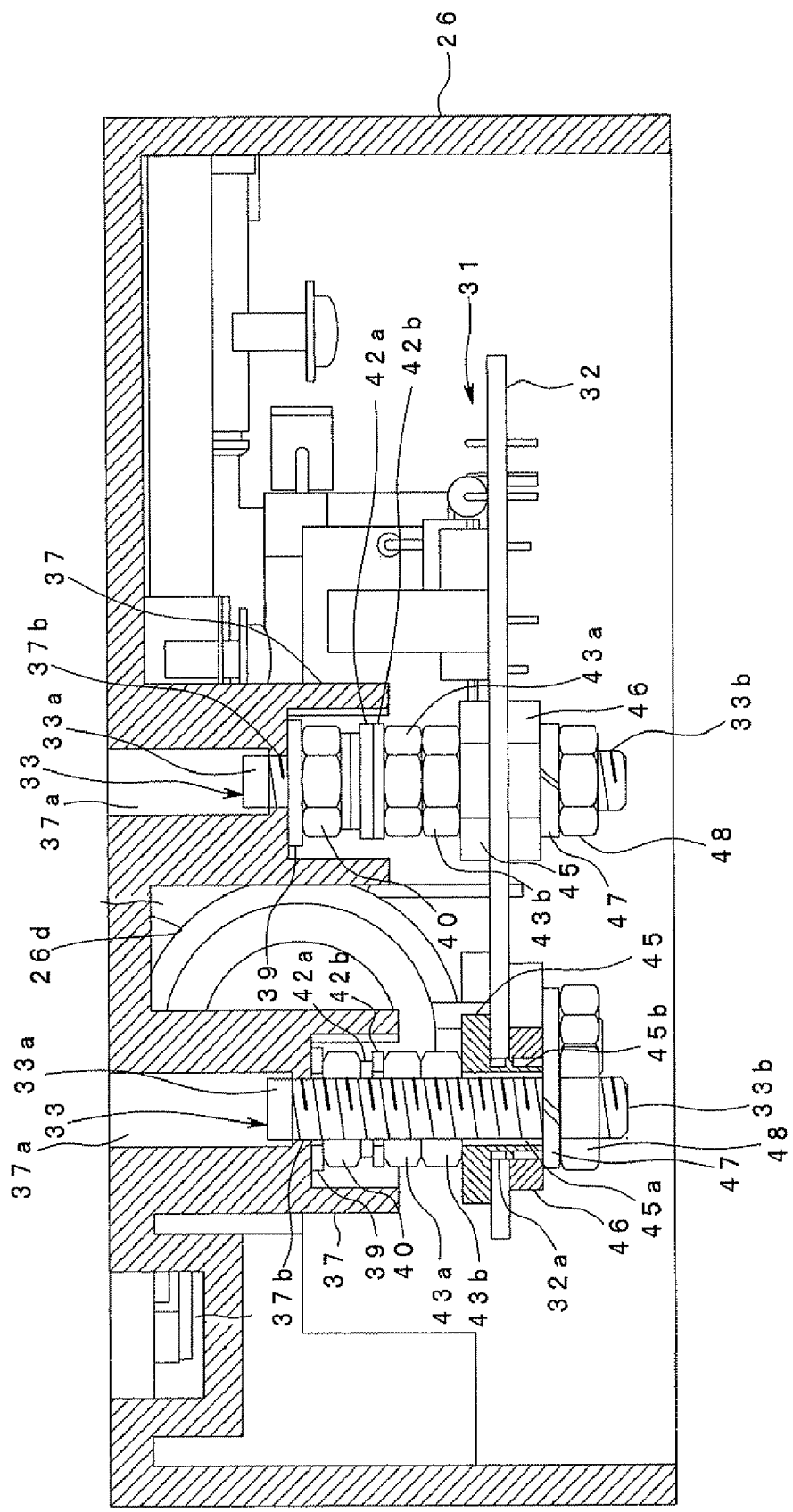

Further, an igniter 31 electrically connected to the power source case 6 is housed in the lamp base 26. The igniter 31 is configured to turn on the discharge lamp by boosting a voltage generated in the power source case 6 to a high voltage and by applying the boosted high voltage to the discharge lamp. As shown in FIG. 14, a substrate (igniter substrate) 32 of the igniter 31 is hangingly provided in the lamp base 26 via a plurality of (three in the present embodiment) support bolts 33.

Further, feeder lines, respectively extended from the negative electrode 35*a* and the positive electrode 35*b* which are provided in the lamp base 26, are connected to the corresponding support bolts 33, respectively. Further, the power source line extended from the power source case 6 is connected to the corresponding other support bolt 33 via the known circuit breaker device connected to the interlock switch provided in the lamp replacement door opening detection switch 21.

In the following, there will be described fastening structures of the respective support bolts 33. Note that the fastening structures of the respective support bolts 33 are almost the same, and hence only the fastening structure of one of the support bolts 33 will be described.

Figure 12:
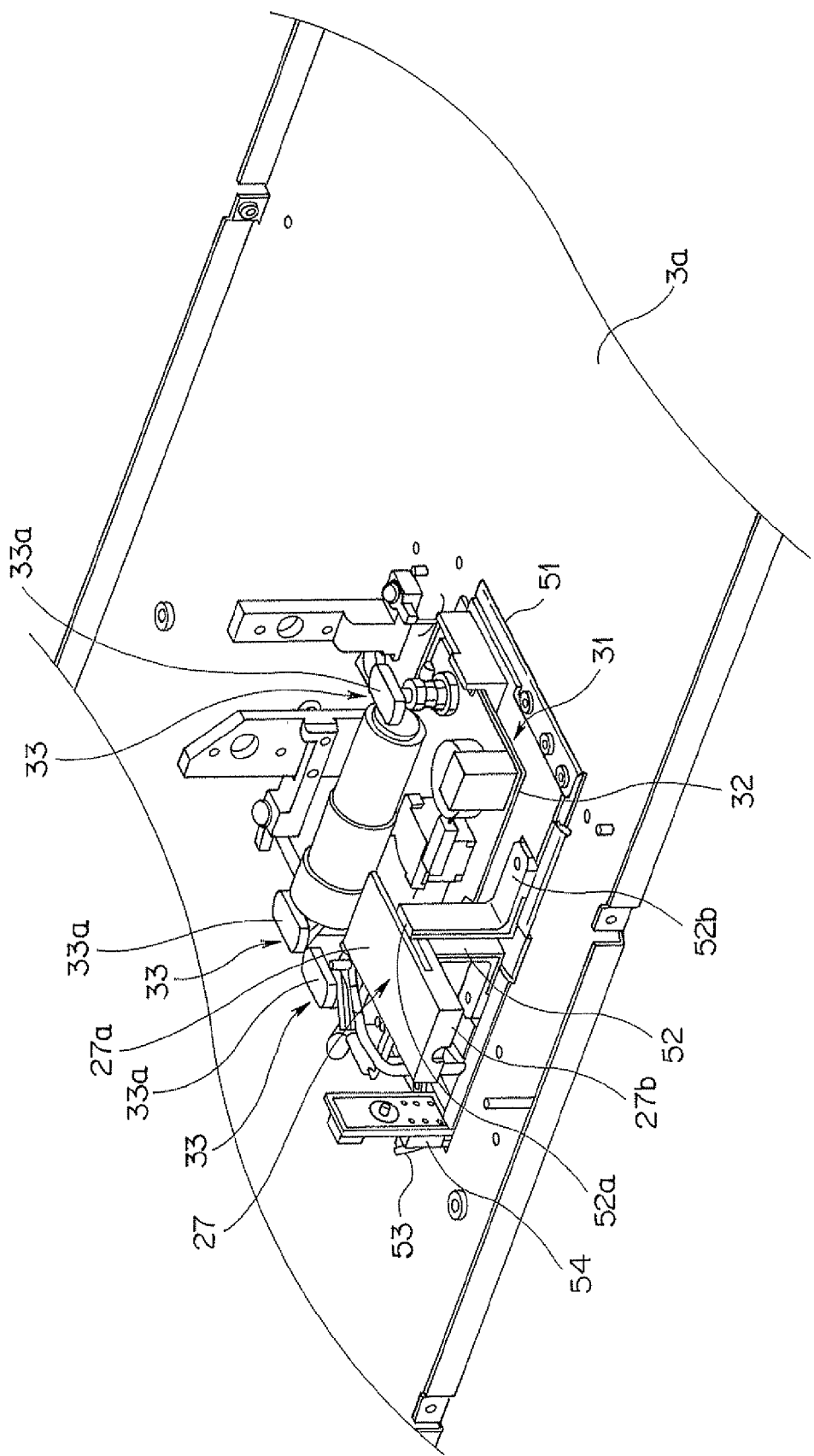

A boss portion 37 is projectingly provided at a position corresponding to the mounting position of each of the support bolts 33 on the ceiling surface 26*d* in the lamp base 26. A bolt hole portion 37*a*, in which a bolt head 33*a* of the support bolt 33 is dropped into, is bored in the boss portion 37. As shown in FIG. 12, the bolt head 33*a* is formed into an elliptic shape, and the inner circumference of the bolt hole portion 37*a* is formed into a rectangular shape so as to be able to house the bolt head 33*a* (see FIG. 10). Therefore, when the bolt head 33*a* is dropped into the bolt hole portion 37*a*, the bolt head 33*a* engages with the inner circumference of the bolt hole portion 37*a*, so that the movement of the bolt head 33*a* in the rotation direction is regulated.

Further, a screw portion insertion hole 37*b* is bored in the bottom portion of the bolt hole portion 37*a*. A first nut 40 is screwed so as to be fastened and fixed, via a washer 39, to a screw portion 33*b* which is made to penetrate the screw portion insertion hole 37*b*. Further, the first and second terminals 42*a* and 42*b* are inserted in the screw portion 33*b* which is made to project downward from the first nut 40, and second and third nuts 43*a* and 43*b* are screwed to the lower surface of the terminal. The second and third nuts 43*a* and 43*b* form a double nut. The first and second terminals 42*a* and 42*b* are pressed to be fixed between the first nut 40, and the second and third nuts 43a and 43b. Further, since the second and third nuts 43a and 43b form the double nut structure, the first to third nuts 40, 43a and 43b are prevented from being loosened, so that poor contact is prevented from being caused in the first and second terminals 42a and 42b. Note that the support bolt 33 and the respective nuts 40, 43a and 43b are formed of a conductive material, such as iron, brass and aluminum.

Further, a hole portion 45a of a contact bolt 45 is inserted into the screw portion 33b which is made to project from the lower end of the third nut 43b. The contact bolt 45, whose screw portion 45b is inserted into a through hole 32a bored in the igniter substrate 32, is fastened by a contact nut 46 screwed into the screw portion 45b projected on the opposite side of the igniter substrate 32. Note that the distal end surface of the screw portion 45b is slightly projected from the contact nut 46.

A land is formed around the through hole 32a bored in the igniter substrate 32. The land is electrically connected to the first and second terminals 42a and 42b via the contact bolt 45, the screw portion 33b of the support bolt 33, and the respective nuts 43a and 43b. Note that the contact bolt 45 is formed of a conductive material, such as iron, brass, and aluminum. A lock nut 48 is fastened, via a spring washer 47, to the screw portion 33b of the support bolt 33 inserted in the hole portion 45a of the contact bolt 45. As described above, the screw portion 45b of the contact bolt 45 is slightly projected from the contact nut 46. Thus, even when the lock nut 48 is strongly fastened, the fastening load is prevented from being applied to the igniter substrate 32, so that the igniter substrate 32 can be effectively protected.

Further, the contact bolt 45 and the contact nut 46 are fastened to each other so as to sandwich the igniter substrate 32 therebetween. Thus, even when the screw portion 33b of the support bolt 33 is extracted from the hole portion 45a of the contact bolt 45, the contact bolt 45 is prevented from dropping out of the igniter substrate 32. Therefore, when the lock nut 48 is loosened, only the igniter substrate 32 is separated from the screw portion 33b of the support bolt 33. Note that there is formed in the igniter substrate 32 an electric circuit which generates a high voltage pulse for turning on the discharge lamp.

Further, an igniter replacement window 3d as a second opening portion, which allows access to the igniter 31 from the outside, is formed in a portion positioned within the inner circumference of the lamp base 26 of the chassis 3a. The igniter replacement window 3d is closed by an igniter replacement door 51 as a second door.

Figure 4:
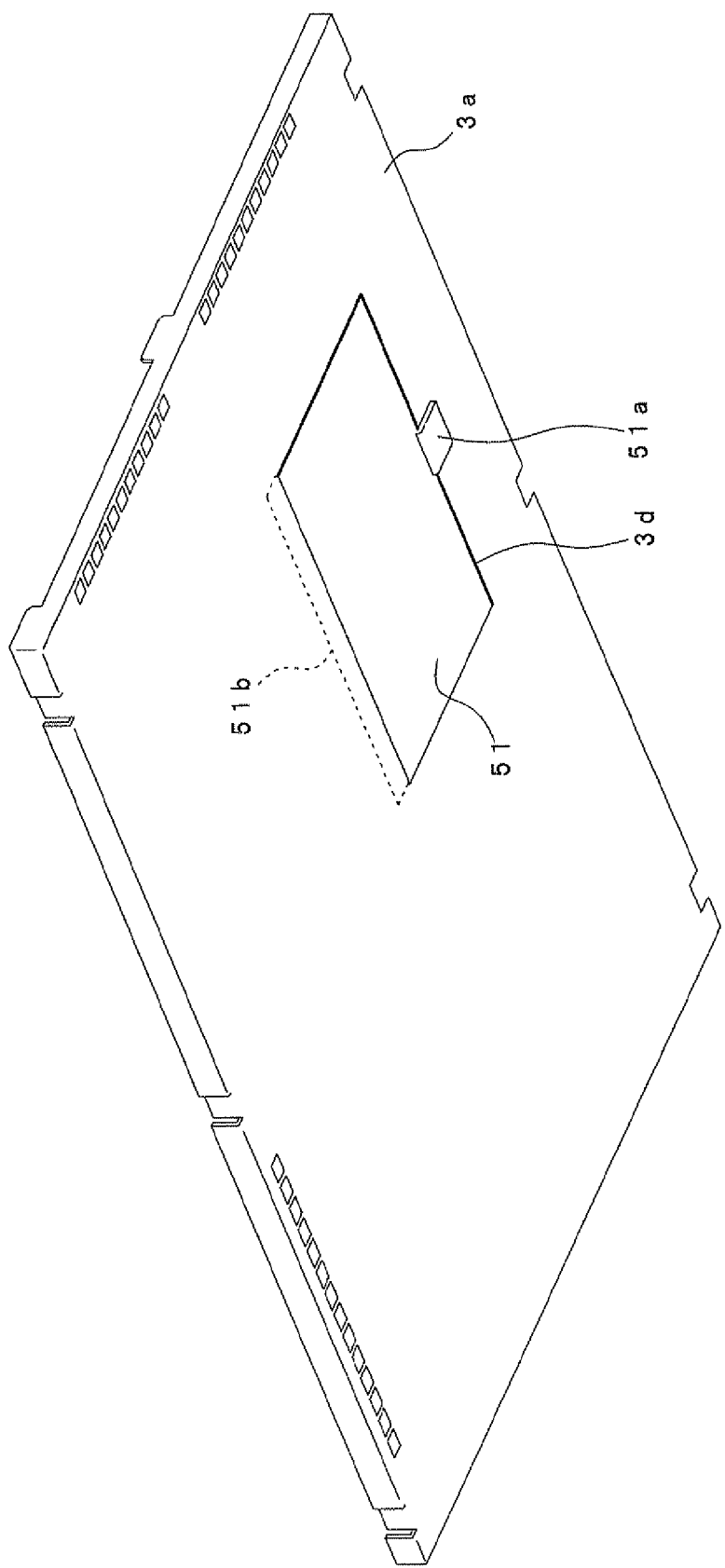

As shown in FIG. 4, FIG. 5 and FIG. 6, a latch piece 51a, which is hooked on the outer surface of the chassis 3a, is bent and formed in one side of the igniter replacement door 51, and a step portion 51b, which is hooked to the inner surface of the chassis 3a via a gasket 55, is bent and formed in the other side facing the one side of the igniter replacement door 51. Note that although not shown, the igniter replacement door 51 is screwed so as to be fixed to the chassis 3a.

Figure 11:
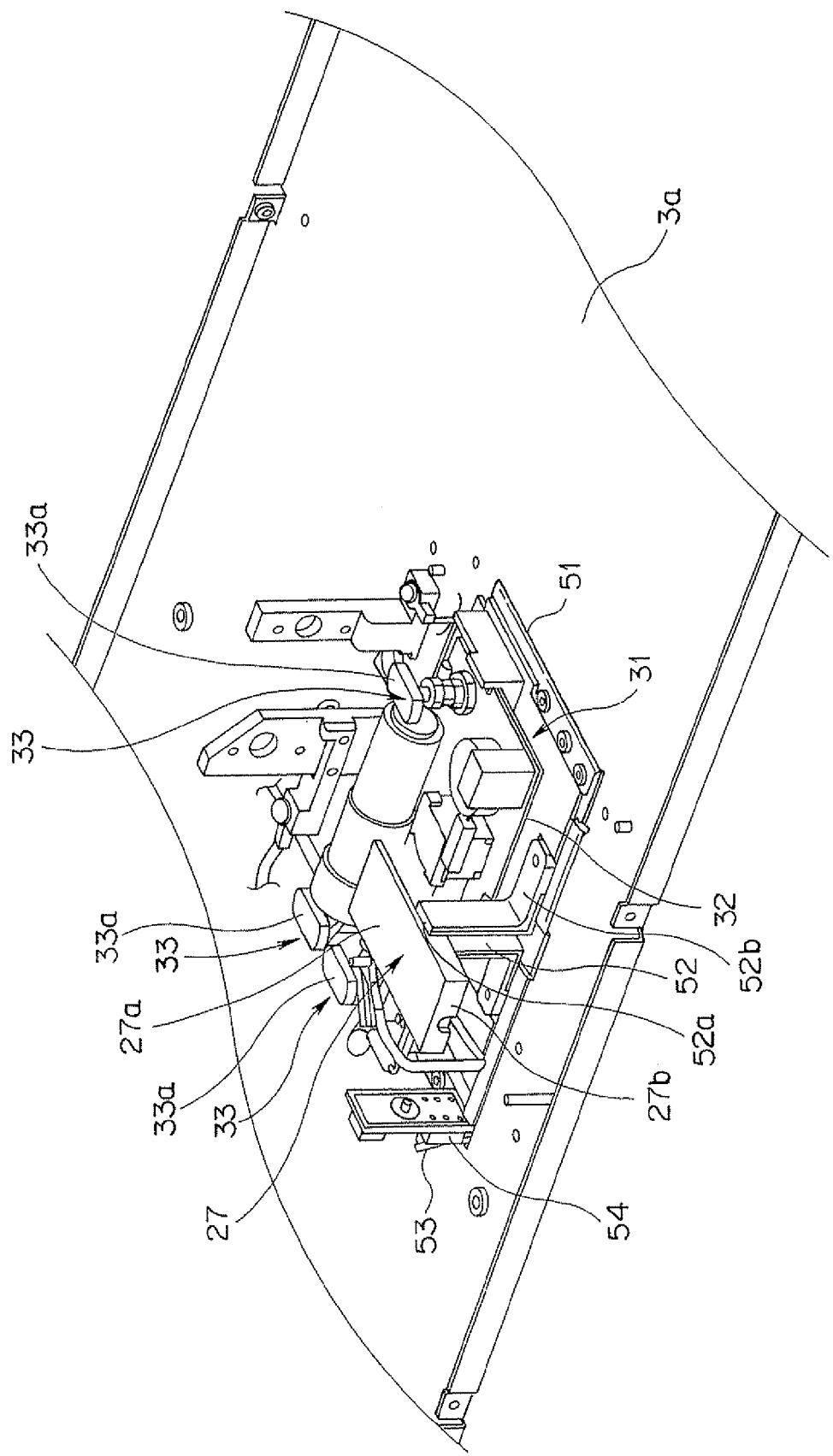

Further, a hook member 52 is vertically erected on the inner surface of the igniter replacement door 51. As shown in FIG. 11 and FIG. 12, the hook member 52 is bent and formed in a hat shape, and has, at the center thereof, a hook portion 52a which engages with the above described claw portion 27f of the slider 27. Further, flange portions 52b bent and formed on both sides of the hook portion 52a are fixed to the inner surface of the igniter replacement door 51. Note that the door opening regulating mechanism, which regulates the opening of the igniter replacement door 51, is configured by the slider 27 and the hook member 52.

As shown in FIG. 6, when the igniter replacement window 3d is closed by the igniter replacement door 51, the hook portion 52a is made to face the direction in which the claw portion 27f formed in the slider 27 is moved. Further, as shown in FIG. 5, in the state where the lamp replacement window 4a is closed by the lamp replacement door 14, the pressing surface 15a of the protection member 15 fixed to the inner surface of the lamp replacement door 14 presses the front surface portion 27b of the slider 27, so as to move the slider 27 into the lamp base 26. Then, the claw portion 27f formed in the slider 27 is engaged with the hook portion 52a, so that the igniter replacement door 51 is locked in the closed state.

Meanwhile, in the present embodiment, the igniter replacement door 51 cannot be removed unless the lamp replacement door 14 is opened, but at the time of mounting, only the lamp replacement door 14 can be attached. Therefore, a switch (igniter replacement door opening detection switch) 54, which detects omission of mounting the igniter replacement door 51, is provided in the light source apparatus 1.

Figure 9:
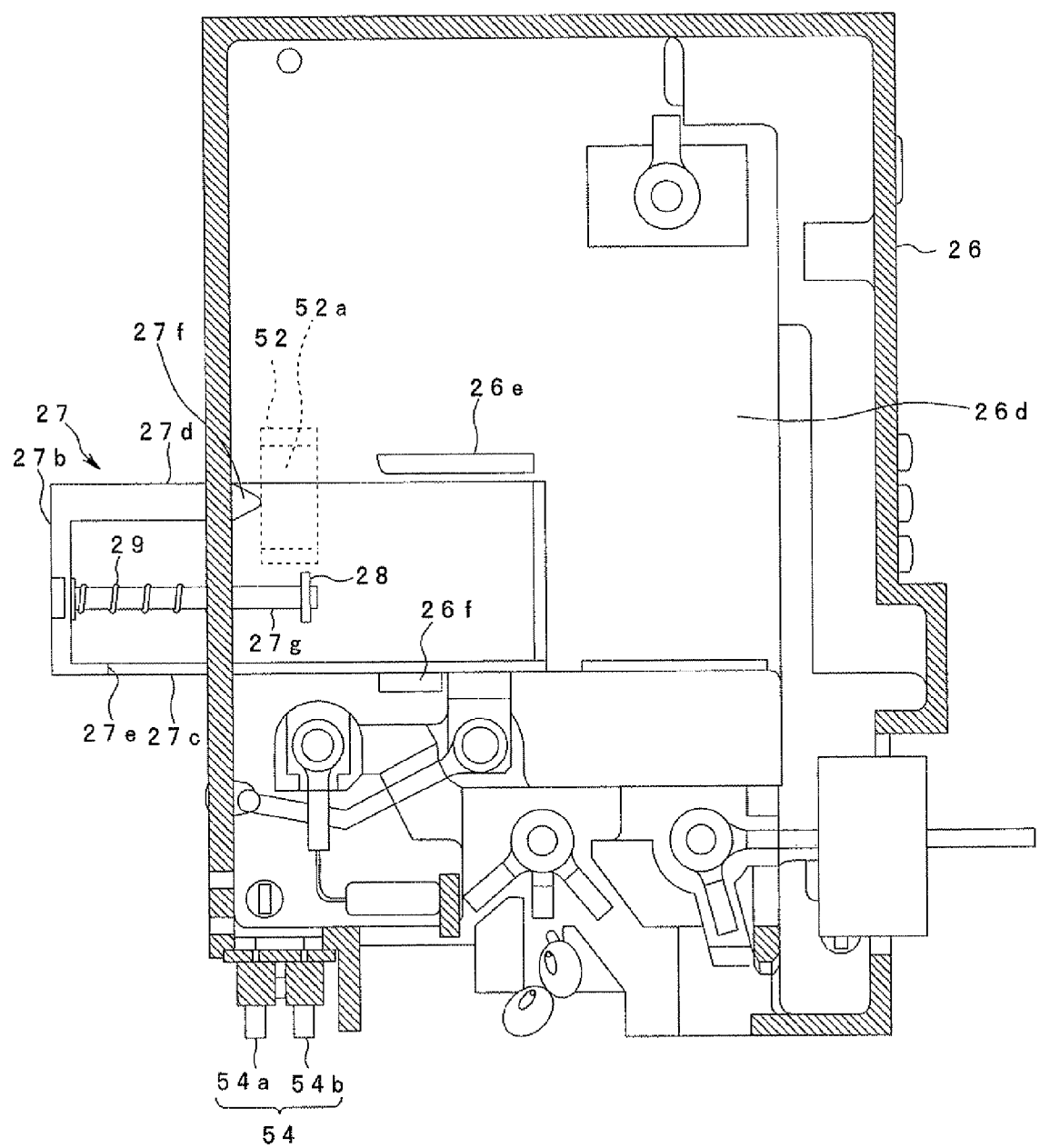
Figure 10:
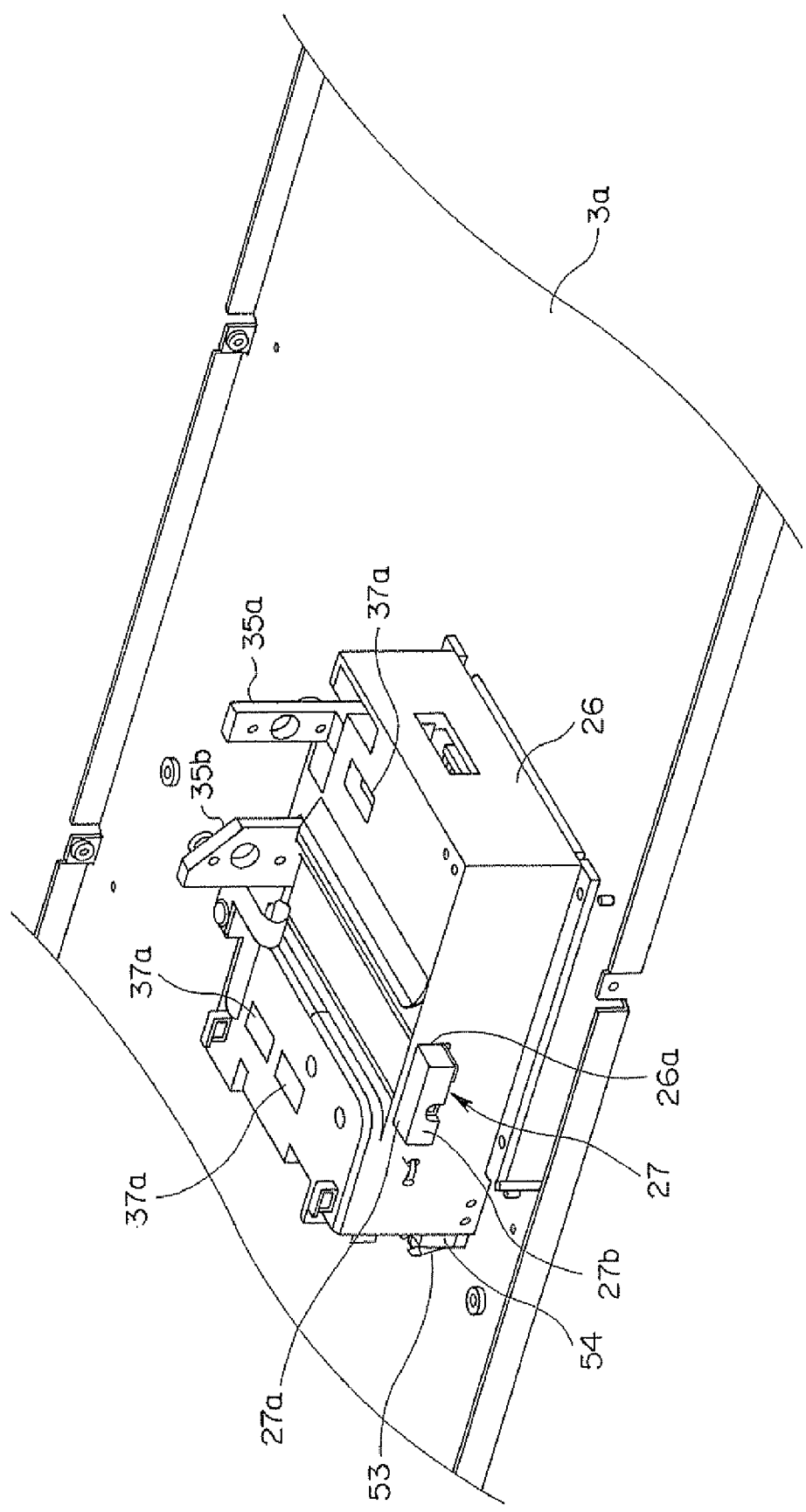

That is, as shown in FIG. 8, FIG. 9 and FIG. 11, the igniter replacement door opening detection switch 54, which detects the opening of the igniter replacement door 51, is fixed to the one side of the lamp base 26. The igniter replacement door opening detection switch 54 is a twin switch having an interlock switch 54a and a discharge switch 54b. In the state where the igniter replacement window 3d is closed by the igniter replacement door 51, the interlock switch 54a and the discharge switch 54b are respectively turned on and turned off by being pressed by a switch pressing member 53 fixed to the inner surface of the igniter replacement door 51. In the state where the interlock switch 54a is turned on, the connected state between the power source case 6 and the internal electric circuit is maintained. Further, the discharging circuit is interrupted because the discharge switch is turned off. On the other hand, when the igniter replacement door 51 is opened and when the pressing force applied to the igniter replacement door opening detection switch 54 by the switch pressing member 53 is released, the interlock switch 54a is turned off, so that the power source circuit is interrupted. Also, the discharge switch 54b is turned on, so that the discharging circuit is connected to make the residual voltage of the electric circuit released.

Further, an insulation sheet 56 is stuck on the inner surface of the igniter replacement door 51. The insulation sheet 56 is to prevent that in the state where the igniter replacement door 51 is closed, a lead wire projected from the rear surface of the igniter substrate 32 is brought into contact with the igniter replacement door 51. In this case, a recessed portion for escaping from the lead wire may be provided in the igniter replacement door 51. A section modulus is increased by forming the recessed portion in the igniter replacement door 51, so that the strength of the igniter replacement door 51 can be increased.

Next, there will be described the effect of the present embodiment based on the above described structure. As shown in FIG. 5, FIG. 8 and FIG. 11, in the state where the lamp replacement window 4a which is opened on the side surface (in the left side surface in the present embodiment) of the top cover 4 of the apparatus main body 2 is closed by the lamp replacement door 14, the pressing surface 15a formed at the distal end of the protection member 15 fixed to the inner surface of the lamp replacement door 14 presses the slider 27 supported by the lamp base 26.

In this state, the claw portion 27f formed in the slider 27 is engaged with the hook member 52 fixed to the igniter replacement door 51 closing the igniter replacement window 3d, so that the igniter replacement door 51 is locked. Therefore, even when the igniter replacement door 51 is attempted to be opened, the igniter replacement door 51 cannot be opened because the hook portion 52*a* is engaged with the claw portion 27*f* of the slider 27.

Further, in the igniter replacement door 51, the step portion 51*b* bent and formed in the side facing the side to which the hook member 52 is fixed, is hooked to the inner surface edge portion of the igniter replacement window 3*d*. Thereby, even when the screw fastening the igniter replacement door 51 is removed, the igniter replacement door 51 maintains the state of closing the igniter replacement window 3*d*.

On the other hand, when the igniter 31 is inspected or replaced, the thumb screw 17 screw-fastening the lamp replacement door 14 is first unscrewed from the apparatus main body 2, to make the lamp replacement door 14 opened. Then, as shown in FIG. 6, the pressing force applied to the front surface portion 27*b* of the slider 27 by the pressing surface 15*a* of the protection member 15 fixed to the inner surface of the lamp replacement door 14, is released. Further, as shown in FIG. 7, the pressing force applied to the switch pressing portion 21*a* of the lamp replacement door opening detection switch 21 by the switch pressing member 16 fixed to the inner surface of the lamp replacement door 14, is released.

When the pressing force to the switch pressing portion 21*a* of the lamp replacement door opening detection switch 21 is released, the interlock switch provided in the lamp replacement door opening detection switch 21 is turned off, so that the power source circuit is interrupted. Also, the discharge switch is turned on, so that the discharging circuit is connected to make the residual voltage of the electric circuit released.

Further, when the pressing force to the front surface portion 27*b* of the slider 27 is released, the slider 27 is made to project from the lamp base 26 to the side of the opening window 5*a* formed in the lamp case 5 by the urging force of the return spring 29. The slider guides 26*e* and 26*f* are arranged on both sides of the slider 27, and the upper surface 27*a* is arranged close to the ceiling surface 26*d* of the lamp base 26. Thus, the slider 27 is smoothly moved by being guided by the slider guides 26*e* and 26*f* and the upper surface 27*a*.

Then, as shown in FIG. 6, FIG. 9 and FIG. 12, the claw portion 27*f* formed in the slider 27 is retreated from the hook portion 52*a* of the hook member 52 fixed to the inner surface of the igniter replacement door 51. This results in the state where the igniter replacement door 51 can be removed.

Then, the screw (not shown), which fastens the igniter replacement door 51 for closing the igniter replacement window 3*d* opened in the bottom surface of the chassis 3*a* of the main body portion 3, is unscrewed. At this time, since the claw portion 27*f* of the slider 27 is retreated from the hook portion 52*a* of the hook member 52, the igniter replacement door 51 can be easily removed. Then, when the igniter replacement door 51 is removed from the igniter replacement window 3*d*, there is released the pressing force applied by the switch pressing member 53 fixed to the inner surface of the igniter replacement door 51, to the interlock switch 54*a* and the discharge switch 54*b* which configure the igniter replacement door opening detection switch 54.

As a result, the interlock switch 54*a* is turned off, and the discharge switch 54*b* is turned on. When the interlock switch 54*a* is turned off, the power source circuit already interrupted is doubly interrupted. On the other hand, when the discharge switch 54*b* is turned on, the discharging circuit is connected by another circuit. Note that when the lamp replacement door 14 is opened, the lamp replacement door opening detection switch 21 is operated, so that the power source circuit already interrupted is interrupted, and that the discharging circuit is connected. Thus, the igniter replacement door opening detection switch 54 may be omitted.

Then, the igniter 31 exposed from the opened igniter replacement window 3*d* is taken out. When the igniter 31 is to be taken out, as shown in FIG. 14, the three lock nuts 48 fastening the igniter substrate 32 are unscrewed from the screw portion 33*b* of the support bolt 33. Then, the igniter substrate 32 is detached from the screw portion 33*b* of the support bolt 33. In this case, the first and second terminals 42*a* and 42*b* are fastened to the support bolt 33 by the double nut mechanism configured by the second and third nuts 43*a* and 43*b*, and hence do not come off even when the lock nut 48 is loosened.

Thereafter, the igniter substrate 32 is taken out from the igniter replacement window 3*d* which is opened in the chassis 3*a*, so as to be subjected to a predetermined inspection. Alternatively, a new igniter substrate 32 is prepared. Then, the igniter substrate 32 subjected to the inspection or the new igniter substrate 32 is housed in the lamp base 26. When the igniter substrate 32 is to be housed in the lamp base 26, the screw portion 33*b* of the support bolt 33 is inserted into the hole portion 45*a* of the contact bolt 45 which is fastened to the through hole 32*a* of the igniter substrate 32 via the contact nut 46. Then, the lock nut 48 is screwed into the screw portion 33*b* projected on the side of the contact nut 46, so as to be fastened.

In this case, since the screw portion 45*b* of the contact bolt 45 is slightly projected from the contact nut 46, even when the lock nut 48 is strongly tightened, the load is transferred only to the second nut 43*b* via the contact bolt 45. Thus, an unnecessary load is not applied to the igniter substrate 32.

Further, in the present embodiment, when the lock nut 48 is loosened, only the igniter substrate 32 is detached, and the fastening state of the first and second terminals 42*a* and 42*b* is maintained. Thereby, the igniter substrate 32 can be easily attached and detached, so that the workability is improved.

Then, after the igniter substrate 32 is attached to the support bolt 33 at a predetermined position, the igniter replacement door 51 is attached to the igniter replacement window 3*d*. Since the insulation sheet 56 is stuck on the inner surface of the igniter replacement door 51, the lead wire projected from the rear surface of the igniter substrate 32 is prevented from being brought into contact with the inner surface of the igniter replacement door 51.

Further, when the igniter replacement door 51 is to be attached to the igniter replacement window 3*d*, the lamp replacement door 14 is not yet attached. Thus, the slider 27 is maintained in the projected state and the claw portion 27*f* is in the retreated state, so that the hook member 52 does not interfere with the slider 27. Thereafter, the igniter replacement door 51 is screwed to the chassis 3*a*, so that the igniter replacement window 3*d* is closed.

Note that when the igniter replacement window 3*d* is closed by the igniter replacement door 51, the switch pressing member 53 presses the igniter replacement door opening detection switch 54. Thereby, the interlock switch 54*a* is turned on, so that the power source circuit is connected. Further, the discharge switch 54*b* is turned off, so that the discharging circuit is interrupted.

Thereafter, the lamp replacement door 14 is attached to the lamp replacement window 4*a*, so as to be fixed to the apparatus main body 2 by the thumb screw 17. Then, the switch pressing member 16 fixed to the inner surface of the lamp replacement door 14 presses the switch pressing portion 21*a* of the lamp replacement door opening detection switch 21 via the leaf spring guide 23. Thereby, the interlock switch is turned on to make the power source circuit connected. Also, the discharge switch is turned off to make the discharging circuit interrupted.

Further, the pressing surface 15*a* of the protection member 15 fixed to the inner surface of the lamp replacement door 14 presses the front surface portion 27*b* of the slider 27, so that the slider 27 is retreated against the urging force of the return spring 29. Then, the claw portion 27*f* formed in the slider 27 is engaged in the hook portion 52*a* of the hook member 52 fixed to the inner surface of the igniter replacement door 51, so that the igniter replacement door 51 is locked in the closed state.

In this way, the present embodiment is configured such that the igniter replacement door 51 is never opened unless the lamp replacement door 14 is opened. Thus, when the lamp replacement door 14 is opened, the interlock switch configuring the lamp replacement door opening detection switch 21 is turned off to make the power source circuit interrupted. Also, the discharge switch is turned on to make the discharging circuit connected. Thus, the interlock switch and the discharge switch on the side of the igniter replacement door 51 need not be provided in principle. Thereby, the reduction in the number of components and the simplification of electrical wiring and structure can be realized, so that the assembling is facilitated.

Further, the first and second terminals 42*a* and 42*b* are fastened to the support bolt 33 supporting the igniter substrate 32, by the double nut mechanism configured by the second and third nuts 43*a* and 43*b*. Thus, even when the igniter substrate 32 is detached from the support bolt 33, the first and second terminals 42*a* and 42*b* are prevented from coming off. Thereby, the igniter substrate 32 can be easily attached and detached, so that the workability is improved.

Second Embodiment

FIG. 15 to FIG. 20 show a second embodiment according to the present invention. Note that components which are the same as those of the first embodiment are denoted by the same reference numerals and characters, and the explanation thereof is omitted.

The above described first embodiment is configured such that even when the igniter replacement door 51 is opened, only the lamp replacement door 14 can be closed. However, the present embodiment is configured such that a door closing regulation mechanism is provided, and that in the state where the igniter replacement door 51 is opened, the closing of the lamp replacement door 14 is prevented by the door closing regulation mechanism.

That is, the door closing regulation mechanism 60 has a guide cylinder portion 61 which is formed integrally with the lamp base 26 in the state of being erected vertically to the lamp base 26. The guide cylinder portion 61 is vertically erected at a position to face the hook portion 52*a* of the hook member 52 in the state where the igniter replacement door 51 is closed. The lower end of the guide cylinder portion 61 is opened in the ceiling surface 26*d* of the lamp base 26.

A stopper main body 62 as a regulation member is inserted in the guide cylinder portion 61 so as to be freely moved forward and backward. The stopper main body 62 has a cylindrical shape, and a flat surface 62*a* is formed on one side along the side surface of the stopper main body 62. A hook portion 62*b* is formed stepwise in the upper portion of the flat surface 62*a*. Further, a curved surface portion 62*c*, which is curved toward the lower end direction from the side of the flat surface 62*a*, is formed in the lower portion of the stopper main body 62. Further, the flat surface 62*a* is arranged so as to face the side of the lamp replacement window 4*a*.

Figure 20:
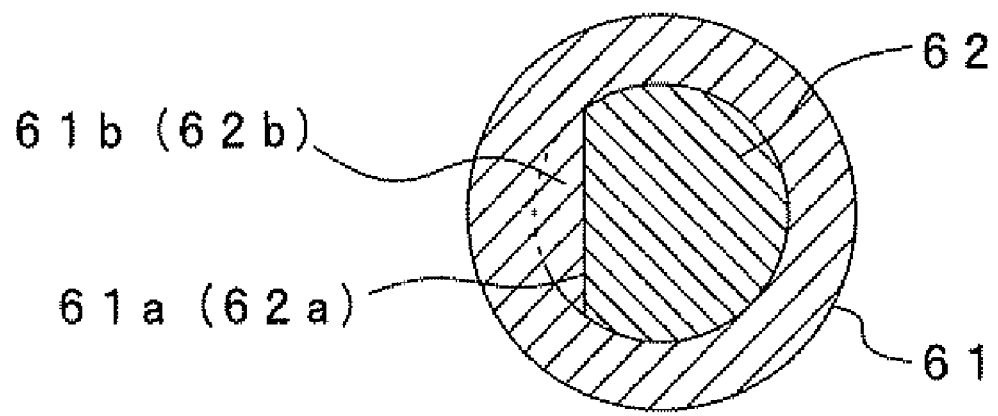

Further, as shown in FIG. 20, the opening portion formed in the ceiling surface 26*d* at the guide cylinder portion 61 is formed in substantially the same shape as the shape of the portion of the stopper main body 62, in which the flat surface 62*a* is formed, that is, in a shape formed by flattening a part of a circular shape. Thereby, the circumferential rotation about the axis of the stopper main body 62 is regulated by the supporting surface 61*a* which is brought into slide contact with the flat surface 62*a*.

Figure 19:
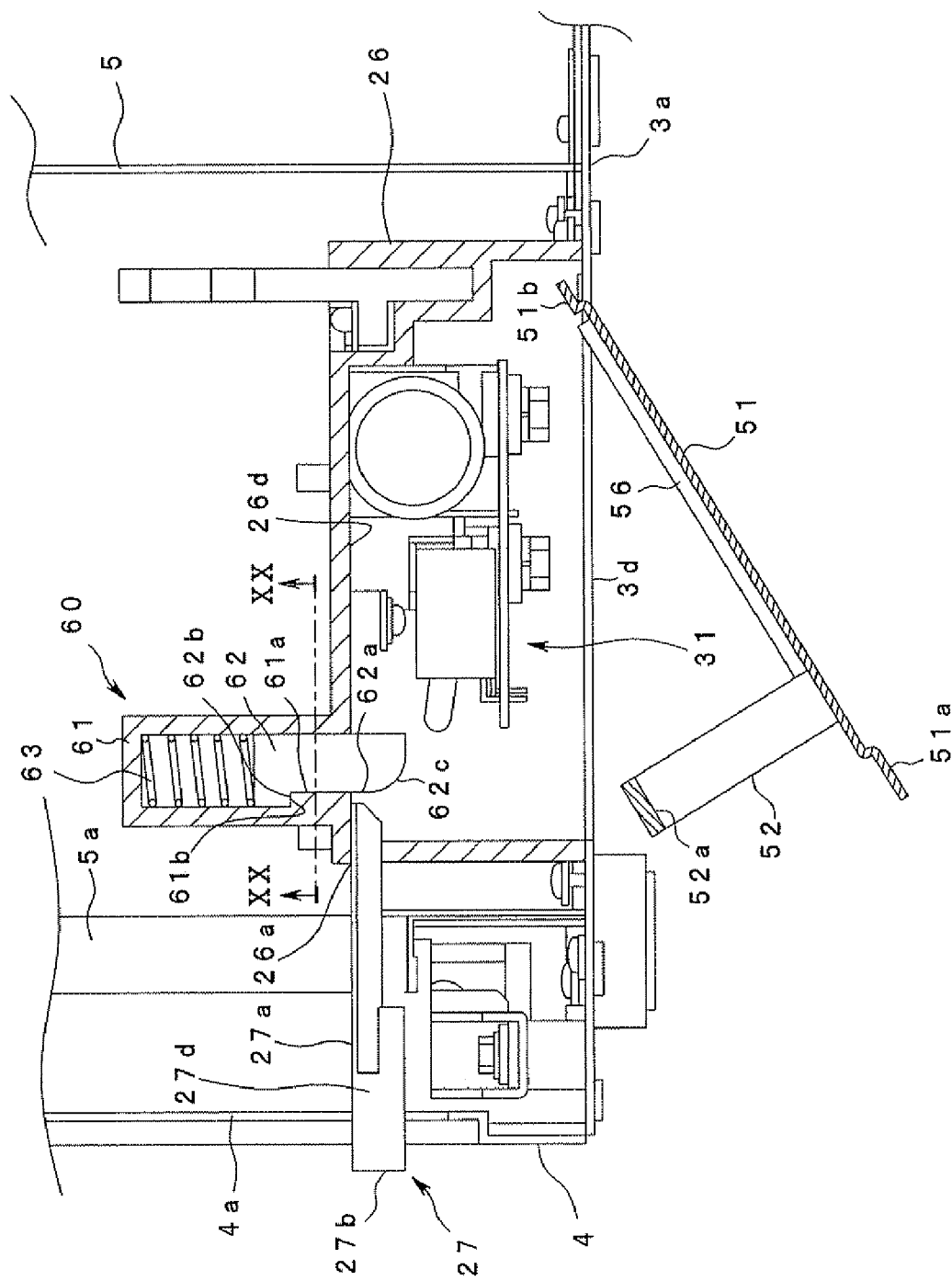

A seat surface 61*b*, which receives the hook portion 62*b* formed in the stopper main body 62, is formed at the upper end of the supporting surface 61*a*. As shown in FIG. 19, in the state where the hook portion 62*b* of the stopper main body 62 is hooked on the seat surface 61*b*, the distal end of the stopper main body 62 is projected downward from the ceiling surface 26*d* of the lamp base 26, so that the distal end of the slider 27 is arranged to face the flat surface 62*a* formed on the stopper main body 62. Further, a compression spring 63, which presses downward the stopper main body 62, is provided between the upper surface of the stopper main body 62 and the internal upper surface of the guide cylinder portion 61.

Figure 17:
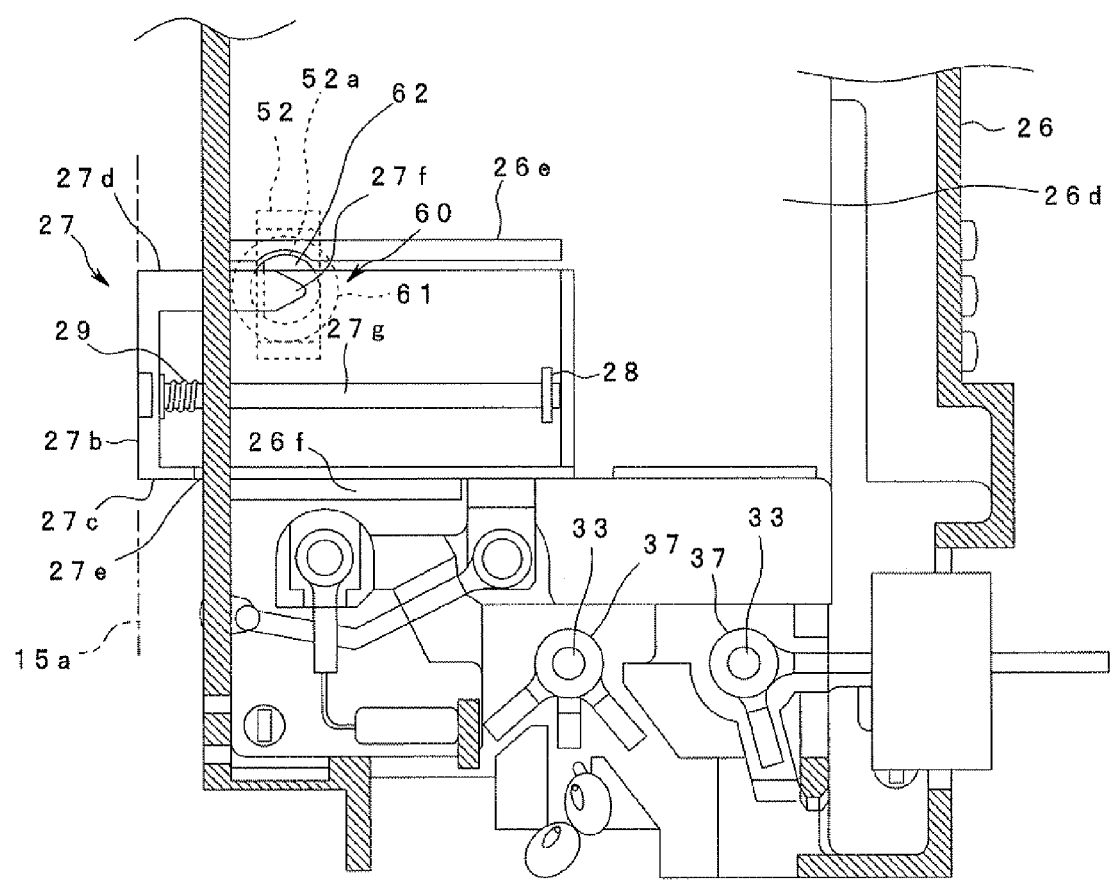
Figure 18:
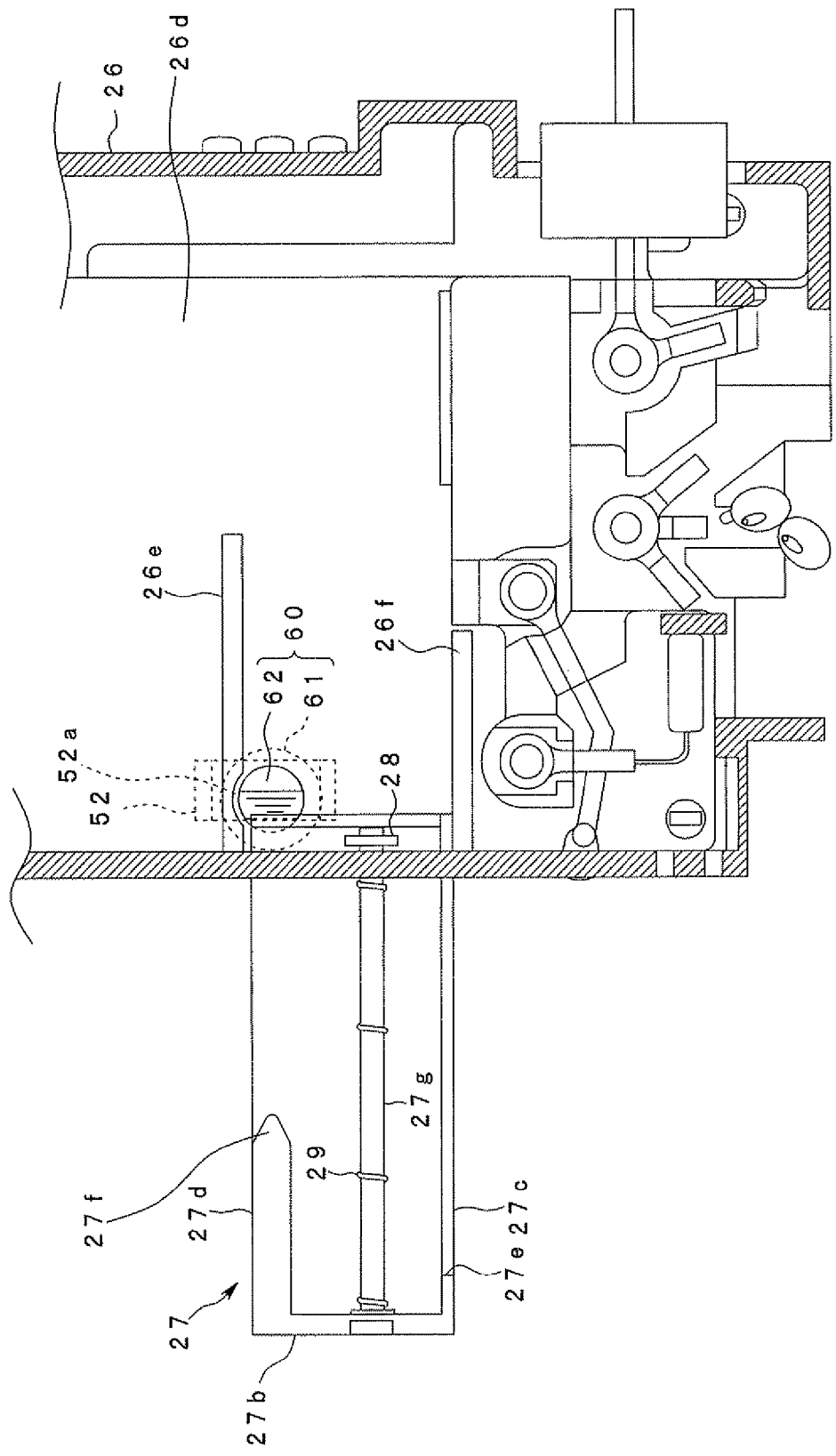

Note that as shown in FIG. 17, the slider guides 26*e* and 26*f* are extended to the inner wall on the side of the guide hole portion 26*a*, and an escape portion is formed at a portion corresponding to the inner circumference of the guide cylinder portion 61. Thereby, as shown in FIG. 18, even when the slider 27 is projected to the outside of the lamp base 26, the movement of the slider 27 in the width direction thereof can be regulated.

Figure 15:
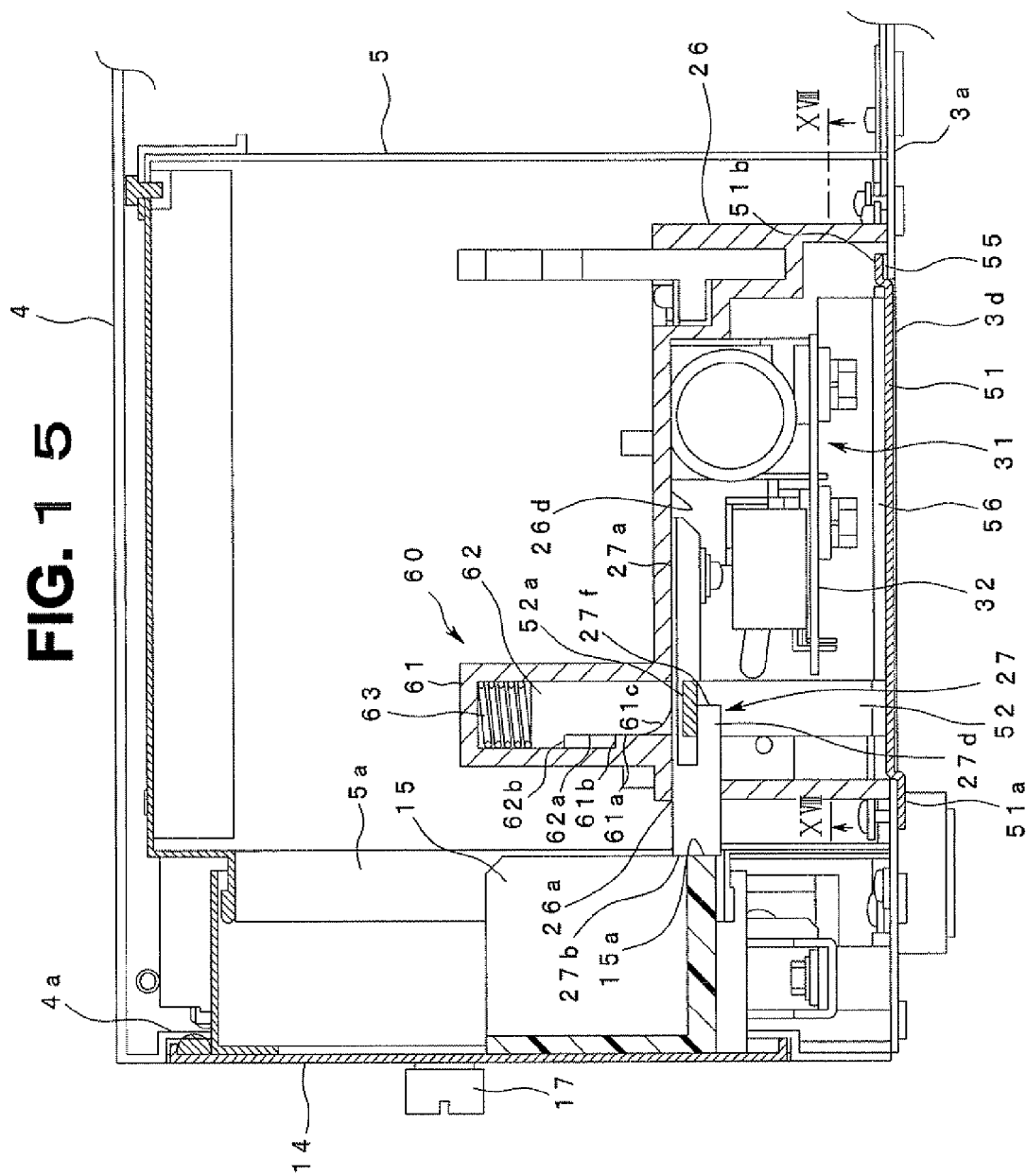

In this configuration, as shown in FIG. 15 and FIG. 17, in the state where both the igniter replacement door 51 and the lamp replacement door 14 are closed, there is maintained a state in which the stopper main body 62 provided in the door closing regulation mechanism 60 is pushed upward by being brought into slide contact with the upper surface 27*a* of the slider 27.

Figure 16:
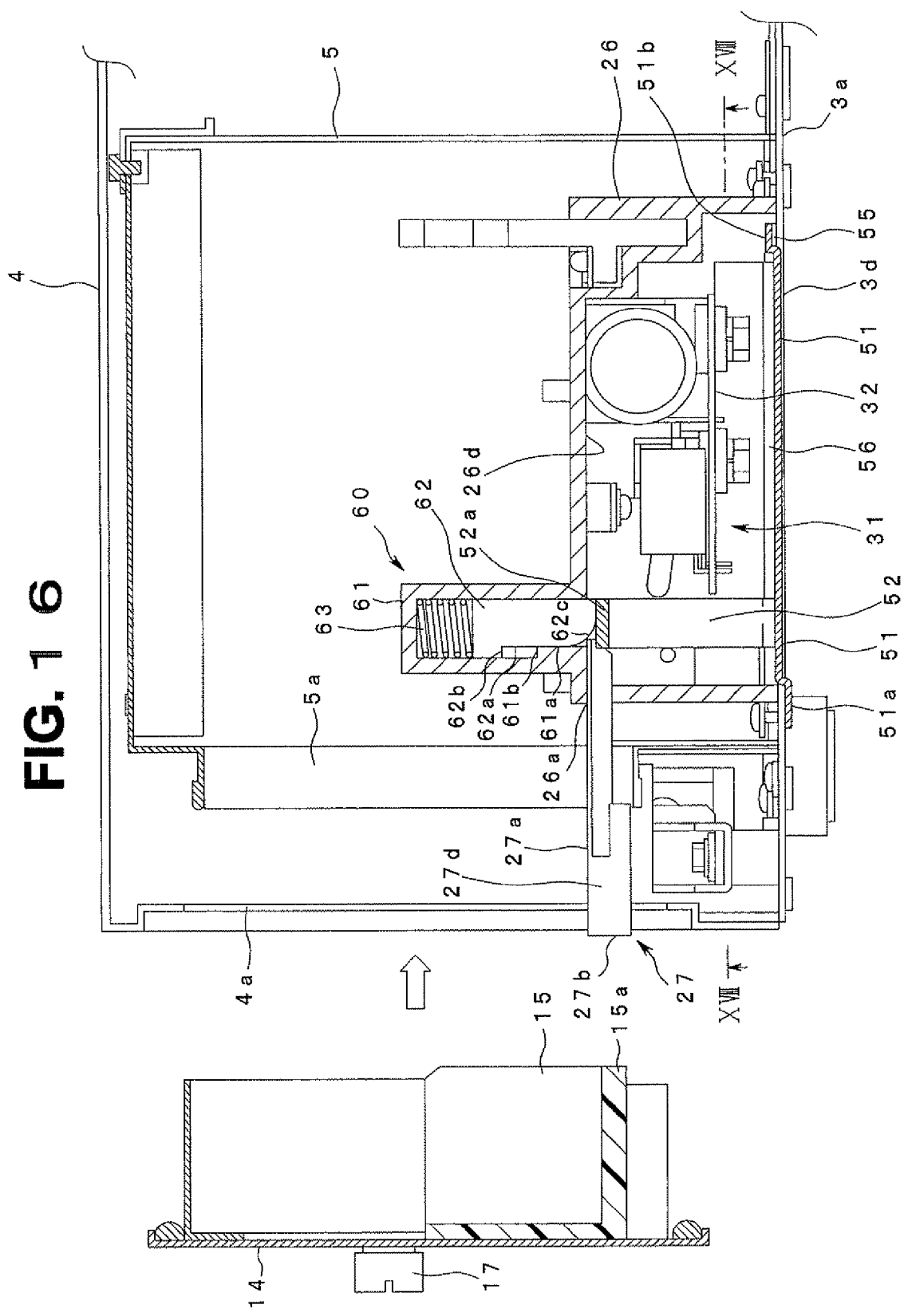

Further, when the lamp replacement door 14 is opened in this state as shown in FIG. 16, the slider 27 is projected by the urging force of the return spring 29 (see FIG. 18), so that the rear end of the slider 27 is separated from the lower end of the stopper main body 62 of the door closing regulation mechanism 60. Thereby, the lower end of the stopper main body 62 is brought into contact with the upper surface of the hook portion 52*a* of the hook member 52 by the urging force of the compression spring 63. Further, the claw portion 27*f* of the slider 27 is separated from the hook portion 52*a* of the hook member 52 fixed to the igniter replacement door 51, and hence the igniter replacement door 51 is permitted to be removed.

Then, as shown in FIG. 19, when the igniter replacement door 51 is opened, the stopper main body 62 is further slid downward by the urging force of the compression spring 63. Thereby, the hook portion 62*b* formed in the stopper main body 62 is hooked on the seat surface 61*b* formed in the guide cylinder portion 61, so that the downward movement is regulated. Then, the flatly formed guide surface 62*a* of the stopper main body 62 is arranged to face the rear end of the slider 27, so that the retreating direction (the movement in the right direction in FIG. 19) of the slider 27 is regulated.

When the lamp replacement door 14 is attempted to be closed without the igniter replacement door 51 being closed in this state, the pressing surface 15*a* of the protection member 15 fixed to the lamp replacement door 14 presses the front surface portion 27*b* of the slider 27. However, the rear end of the slider 27 is brought into contact with the guide surface 62*a* of the stopper main body 62 so that the movement of the slider 27 is regulated. Thus, the lamp replacement door 14 cannot be closed.

On the other hand, when the igniter replacement door 51 is closed, the distal end of the stopper main body 62 is pushed up by the upper surface of the hook portion 52a of the hook member 52 fixed to the igniter replacement door 51 against the urging force of the compression spring 63. Therefore, in this case, the hook portion 52a functions as a pressing portion.

Then, as shown in FIG. 16, when the igniter replacement door 51 is closed, the curved surface portion 62c of the stopper main body 62, the lower end of whose curved surface portion is brought into contact with the hook portion 52a, is arranged to face the rear end of the slider 27.

Therefore, when the lamp replacement door 14 is closed in this state, the pressing surface 15a of the protection member 15 presses the front surface portion 27b of the slider 27, so as to make the slider 27 retreat. Then, the rear end of the slider 27 pushes up the curved surface portion 62c of the stopper main body 62, to make the stopper main body 62 retreat to the position which permits the lamp replacement door 14 to be closed. Also, the rear end of the slider 27 enters between the hook portion 52a and the lower end of the stopper main body 62, to permit the slider 27 to easily retract. As a result, the lamp replacement door 14 can be closed.

In this way, in the present embodiment, there is provided the stopper main body 62 which is pushed up by the hook member 52 fixed to the igniter replacement door 51. Thereby, in the state where the igniter replacement door 51 is opened, the closing of the lamp replacement door 14 is regulated, so that it is possible to prevent the closing of the igniter replacement door 51 from being forgotten. Therefore, in the present embodiment, it is possible to eliminate the igniter replacement door opening detection switch 54 which is provided in the lamp base 26 in the first embodiment.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A light source apparatus comprising:
an apparatus main body;
a first opening portion provided in the apparatus main body, and a first door configured to open and close the first opening portion;
a second opening portion provided in the apparatus main body at a position different from the position of the first opening portion, and a second door configured to open and close the second opening portion;
an opening and closing detecting portion configured to detect the opening and closing of the first door;
a circuit breaker device configured, when the opening state of the first door is detected by the opening and closing detecting portion, to interrupt power supply to a circuit in the apparatus main body;
a door opening regulation mechanism configured, when the closing state of the first door is detected by the opening and closing detecting portion, to lock the closing state of the second door, and configured, when the opening state of the first door is detected by the opening and closing detecting portion, to permit the opening of the second door; and
a door closing regulation mechanism configured to regulate the closing of the first door in the state where the second door is opened, and configured to permit the closing of the first door in the state where the second door is closed.

2. The light source apparatus according to claim 1, wherein the door closing regulation mechanism includes a regulation member configured to be movable from a position at which the closing of the first door is regulated, to a position at which the closing of the first door is not regulated, and a pressing portion provided in the second door, and wherein in the state where the second door is closed, the pressing portion presses the regulation member to make the regulation member retreat to a position at which the closing of the first door is permitted.

3. The light source apparatus according to claim 1,
wherein a discharge lamp and an igniter configured to turn on the discharge lamp are provided in the apparatus main body,
wherein the first opening portion configured to be closed by the first door is opened at a position at which the discharge lamp can be accessed, and
wherein the second opening portion configured to be closed by the second door is opened at a position at which the igniter can be accessed.

4. The light source apparatus according to claim 2,
wherein a discharge lamp and an igniter configured to turn on the discharge lamp are provided in the apparatus main body,
wherein the first opening portion configured to be closed by the first door is opened at a position at which the discharge lamp can be accessed, and
wherein the second opening portion configured to be closed by the second door is opened at a position at which the igniter can be accessed.

5. The light source apparatus according to claim 1, wherein the door opening regulation mechanism is operated in linkage with the first door, to lock the closing state of the second door in the state where the first door is closed.

6. The light source apparatus according to claim 1, wherein the door opening regulation mechanism is operated in linkage with the first door, to lock the closing state of the second door in the state where the first door is closed.

7. The light source apparatus according to claim 2, wherein the door opening regulation mechanism is operated in linkage with the first door, to lock the closing state of the second door in the state where the first door is closed.

8. The light source apparatus according to claim 3, wherein the door opening regulation mechanism is operated in linkage with the first door, to lock the closing state of the second door in the state where the first door is closed.

9. The light source apparatus according to claim 4, wherein the door opening regulation mechanism is operated in linkage with the first door, to lock the closing state of the second door in the state where the first door is closed.

10. The light source apparatus according to claim 1,
wherein the door opening regulation mechanism includes a slider provided in the apparatus main body and configured to be pressed by the first door, and
wherein in the state where the first door is closed, the slider is pressed and moved to lock the closing state of the second door.

11. The light source apparatus according to claim 1, wherein the door opening regulation mechanism includes a slider provided in the apparatus main body and configured to be pressed by the first door, and wherein in the state where the first door is closed, the slider is pressed and moved to lock the closing state of the second door.

12. The light source apparatus according to claim 2,
wherein the door opening regulation mechanism includes a slider provided in the apparatus main body and configured to be pressed by the first door, and
wherein in the state where the first door is closed, the slider is pressed and moved to lock the closing state of the second door.

13. The light source apparatus according to claim 3,
wherein the door opening regulation mechanism includes a slider provided in the apparatus main body and configured to be pressed by the first door, and
wherein in the state where the first door is closed, the slider is pressed and moved to lock the closing state of the second door.

14. The light source apparatus according to claim 1, wherein the first opening portion is formed in the side surface of the apparatus main body, and wherein the second opening portion is formed in the bottom surface of the apparatus main body.

15. The light source apparatus according to claim 2, wherein the first opening portion is formed in the side surface of the apparatus main body, and wherein the second opening portion is formed in the bottom surface of the apparatus main body.

* * * * *